United States Patent
Allen et al.

(10) Patent No.: US 9,493,391 B2
(45) Date of Patent: Nov. 15, 2016

(54) PROCESS FOR BETA-LACTONE PRODUCTION

(71) Applicant: Novomer, Inc., Ithaca, NY (US)

(72) Inventors: Scott D. Allen, Ithaca, NY (US); Ronald R. Valente, Ithaca, NY (US); Han Lee, Ithaca, NY (US); Anna E. Cherian, Ithaca, NY (US); Donald L. Bunning, Charleston, WV (US); Nye A. Clinton, Hurricane, WV (US); Olan Stanley Fruchey, Hurricane, WV (US); Bernard Duane Dombek, Charleston, WV (US)

(73) Assignee: NOVOMER, INC., Ithaca, NY (US)

( * ) Notice: Subject to any disclaimer, the term of this patent is extended or adjusted under 35 U.S.C. 154(b) by 0 days.

(21) Appl. No.: 14/857,313

(22) Filed: Sep. 17, 2015

(65) Prior Publication Data

US 2016/0102040 A1    Apr. 14, 2016

Related U.S. Application Data

(63) Continuation of application No. 14/275,139, filed on May 12, 2014, now Pat. No. 9,206,144, which is a continuation of application No. 13/860,179, filed on Apr. 10, 2013, now Pat. No. 8,796,475, which is a continuation of application No. 13/262,985, filed as application No. PCT/US2010/030230 on Apr. 7, 2010, now Pat. No. 8,445,703.

(60) Provisional application No. 61/310,257, filed on Mar. 3, 2010, provisional application No. 61/286,382, filed on Dec. 15, 2009, provisional application No. 61/167,711, filed on Apr. 8, 2009.

(51) Int. Cl.

| | |
|---|---|
| C07C 51/377 | (2006.01) |
| C08G 63/08 | (2006.01) |
| C07C 67/317 | (2006.01) |
| C07C 231/14 | (2006.01) |
| C07D 305/12 | (2006.01) |
| C07D 307/60 | (2006.01) |
| C07C 51/09 | (2006.01) |
| C07C 67/30 | (2006.01) |

(52) U.S. Cl.
CPC ............ *C07C 51/377* (2013.01); *C07C 51/09* (2013.01); *C07C 67/30* (2013.01); *C07C 67/317* (2013.01); *C07C 231/14* (2013.01); *C07D 305/12* (2013.01); *C07D 307/60* (2013.01); *C08G 63/08* (2013.01); *Y02P 20/584* (2015.11)

(58) Field of Classification Search
None
See application file for complete search history.

(56) References Cited

U.S. PATENT DOCUMENTS

| | | |
|---|---|---|
| 2,469,704 A | 5/1949 | Stone |
| 3,002,017 A | 9/1961 | Wearsch et al. |
| 3,326,938 A | 6/1967 | Wagner |
| 3,751,435 A | 8/1973 | Van der Ven et al. |
| 4,590,293 A | 5/1986 | Pascoe |
| 4,873,378 A | 10/1989 | Murphy et al. |
| 6,084,124 A | 7/2000 | Slaugh et al. |
| 6,392,078 B1 | 5/2002 | Ryu et al. |
| 6,852,865 B2 | 2/2005 | Coates et al. |
| 6,916,951 B2 | 7/2005 | Tustin et al. |
| 7,420,064 B2 | 9/2008 | Luinstra et al. |
| 8,445,703 B2 | 5/2013 | Allen et al. |
| 8,796,475 B2 | 8/2014 | Allen et al. |
| 9,096,510 B2 | 8/2015 | Porcelli et al. |
| 9,206,144 B2 | 12/2015 | Allen et al. |
| 2003/0098274 A1 | 5/2003 | Lee et al. |
| 2003/0162961 A1 | 8/2003 | Coates et al. |
| 2003/0212295 A1 | 11/2003 | Charles et al. |
| 2005/0014977 A1 | 1/2005 | Drent et al. |
| 2005/0222458 A1 | 10/2005 | Craciun et al. |
| 2005/0240032 A1 | 10/2005 | Luinstra et al. |
| 2005/0256320 A1 | 11/2005 | Luinstra et al. |
| 2007/0217965 A1 | 9/2007 | Johnson et al. |
| 2007/0293695 A1 | 12/2007 | Zoeller et al. |
| 2009/0124787 A1 | 5/2009 | Preishuber-Pflugl et al. |
| 2009/0253934 A1 | 10/2009 | Ho et al. |
| 2012/0123137 A1 | 5/2012 | Allen et al. |
| 2013/0281715 A1 | 10/2013 | Allen et al. |
| 2014/0275575 A1 | 9/2014 | Allen et al. |
| 2014/0309399 A1 | 10/2014 | Porcelli et al. |

(Continued)

FOREIGN PATENT DOCUMENTS

| | | |
|---|---|---|
| EP | 0352850 A1 | 1/1990 |
| EP | 0441447 A1 | 8/1991 |

(Continued)

OTHER PUBLICATIONS

Communication pursuant to Rule 114(2) EPC, Third Party Observation for application No. EP20100762365, Publication EP2417182, 130 pages (Oct. 2, 2014).
Extended European Search Report for EP10762368.8, 11 pages (Oct. 31, 2012).
International Preliminary Report on Patentability for PCT/US10/30230, 13 pages (Aug. 18, 2011).
International Search Report for PCT/US2010/030230, 3 pages (Jun. 10, 2010).
International Search Report for PCT/US2011/049125, 3 pages (Jan. 11, 2012).
International Search Report for PCT/US2012/061791, 3 pages (Feb. 8, 2013).

(Continued)

*Primary Examiner* — Timothy R Rozof
(74) *Attorney, Agent, or Firm* — Morrison & Foerster LLP

(57) ABSTRACT

The present application provides a method for producing an beta-lactone product. The method includes the steps of: reacting an epoxide, a solvent with a carbonylation catalyst and carbon monoxide to produce a reaction stream comprising a beta-lactone then separating a portion of the beta-lactone in the reaction stream from the solvent and carbonylation catalyst to produce: i) a beta-lactone stream with the beta-lactone, and ii) a catalyst recycling stream including the carbonylation catalyst and the high boiling solvent; and adding the catalyst recycling stream to the feed stream.

39 Claims, 13 Drawing Sheets

(56) References Cited

U.S. PATENT DOCUMENTS

2015/0141693 A1 5/2015 Allen et al.
2015/0299083 A1 10/2015 Porcelli et al.

FOREIGN PATENT DOCUMENTS

| EP | 0 577 206 A2 | 1/1994 |
| EP | 2325214 A1 | 5/2011 |
| JP | 2006-065223 A | 3/2006 |
| JP | 2009-169753 A | 7/2009 |
| WO | WO-03/050154 A2 | 6/2003 |
| WO | WO-03/093211 A1 | 11/2003 |
| WO | WO-2004/012860 A1 | 2/2004 |
| WO | WO-2004/012861 A1 | 2/2004 |
| WO | WO-2005/087699 A1 | 9/2005 |
| WO | WO-2007/047225 A1 | 4/2007 |
| WO | WO-2008/144008 A1 | 11/2008 |
| WO | WO-2010/118128 A1 | 10/2010 |
| WO | WO-2012/030619 A1 | 3/2012 |
| WO | WO-2013/063191 A1 | 5/2013 |
| WO | WO-2013/122905 A1 | 8/2013 |
| WO | WO-2013/126375 A1 | 8/2013 |
| WO | WO-2014/008232 A2 | 1/2014 |

OTHER PUBLICATIONS

International Search Report for PCT/US2013/025683, 2 pages (Apr. 23, 2013).
International Search Report for PCT/US2013/026810, 2 pages (Apr. 3, 2013).
International Search Report for PCT/US2013/049026, 2 pages (Dec. 17, 2013).
Janke, D. et al., Poly-beta-hydroxybutyrate Pilot Plant, Senior Design Projects, Engineering Department Glavin College (May 13, 2005), 127 pages [URL: https://www.calvin.edu/academic/engineering/senior-design/SeniorDesign04-05/Final%20Reports/16-FinalReport.pdf] Retrieved Sep. 9, 2015.
Rowley, J.M., et al., Catalytic Double Carbonylation of Epoxides to Succinic Anhydrides: Catalyst Discovery, Reaction Scope, and Mechanism, Journal of American Chemical Society, 129:4948-4960 (2007).
Slowik, et al., Catalytic conversion of waste carbon monoxide to valuable chemicals & materials, Technical Proceedings of the 2010 Clean Technology Confrence and Trade Show, 283-286 (2010).
Written Opinion for PCT/US12/61791, 6 pages (Feb. 8, 2013).
Written Opinion for PCT/US2010/030230, 13 pages (Jun. 10, 2010).
Written Opinion for PCT/US2011/049125, 10 pages (Jan. 11, 2012).
Written Opinion for PCT/US2013/025683, 10 pages (Apr. 23, 2013).
Written Opinion for PCT/US2013/026810, 9 pages (Apr. 3, 2013).
Written Opinion for PCT/US2013/049026, 6 pages (Dec. 17, 2013).

PROCESS FOR BETA-LACTONE PRODUCTION

CROSS-REFERENCE TO RELATED APPLICATIONS

The present application is a continuation of U.S. patent application Ser. No. 14/275,139, filed May 12, 2014 (now U.S. Pat. No. 9,206,144), which is a continuation of U.S. patent application Ser. No. 13/860,179, filed Apr. 10, 2013 (now U.S. Pat. No. 8,796,475), which is a continuation of U.S. patent application Ser. No. 13/262,985, filed Oct. 5, 2011 (now U.S. Pat. No. 8,445,703), which is the National Stage application under 35 U.S.C. §371 of International Application No.: PCT/US10/30230, filed Apr. 7, 2010, and claims priority to U.S. Provisional Application Ser. Nos.61/167,711, filed Apr. 8, 2009, 61/286,382, filed Dec. 15, 2009, and 61/310,257 filed Mar. 3, 2010, the contents of each of which are hereby incorporated herein by reference.

BACKGROUND OF THE INVENTION

Beta-lactones are useful intermediates in the synthesis of other chemical compounds including acrylic acid and acrylates. Acrylic acid is used as a precursor in a wide variety of chemical industries. Acrylic acid is typically produced from a feedstock of propene, which is itself a byproduct of ethylene and gasoline production. Economic and environmental circumstances have lead to interest in other methods of production of acrylic acid and other acrylates from a variety of feedstocks. Additional feedstocks can include epoxides.

SUMMARY OF THE INVENTION

In various aspects, the present invention provides a method including the steps of reacting the contents of a feed stream including an epoxide, a solvent with a carbonylation catalyst and carbon monoxide to produce a reaction product stream including a beta-lactone, separating a portion of the beta-lactone in the reaction product stream from the solvent and carbonylation catalyst to produce: i) a beta-lactone stream with the beta-lactone, and ii) a catalyst recycling stream including the carbonylation catalyst; and adding the catalyst recycling stream to the feed stream.

In some embodiments, the method further includes treating the beta-lactone stream under conditions to convert the beta lactone into a compound selected from the group consisting of: acrylic acid, methyl acrylate, ethyl acrylate, n-butyl acrylate, isobutyl acrylate, 2-ethylhexyl acrylate.

In some embodiments, the solvent has a boiling point higher than the boiling point of the beta-lactone, at the same pressure. In some embodiments, the solvent has a boiling point lower than the boiling point of the beta-lactone, at the same pressure.

In some embodiments, the beta-lactone stream includes a portion of the solvent and/or the carbonylation catalyst. In some embodiments, the beta-lactone stream includes a portion of the epoxide. In some embodiments, the recycling stream comprises beta-lactone. In some embodiments, the reaction product stream comprises a portion of the epoxide.

In some embodiments, the reaction product stream comprises sufficient epoxide to prevent anhydride formation. In some embodiments, the reaction product stream comprises at least about 10% epoxide, at least about 5% epoxide, at least about 3% epoxide, or at least about 0.1% epoxide.

In some embodiments, the reaction product stream comprises less than about 5% anhydride, or less than about 1% anhydride. In some embodiments, the reaction product stream is essentially free of anhydride.

In some embodiments, the method further includes treating the catalyst recycling stream, prior to the adding step by performing at least one step selected from the group consisting of: adding fresh carbonylation catalyst, removing spent carbonylation catalyst; adding solvent; adding epoxide, adding a portion of the beta-lactone stream; and any combination of two or more of these.

In some embodiments, the separating step comprises volatilizing a portion of the beta-lactone from the reaction product stream. In some embodiments, the separating step includes exposing the reaction product stream to reduced pressure. In some embodiments, the reduced pressure is between about 5 Torr and about 500 Torr. In some embodiments, the reduced pressure is between about 10 Torr and about 100 Torr. In some embodiments, the reduced pressure is sufficient to reduce the boiling point of the beta-lactone by about 20 to about 100° C. below its boiling point at atmospheric pressure.

In some embodiments, the separating step comprises exposing the reaction product stream to elevated temperature. In some embodiments, the elevated temperature is greater than the boiling point of the beta-lactone but less than the boiling point of the solvent.

In some embodiments, the separating step comprises exposing the reaction product stream to reduced pressure and elevated temperature.

In some embodiments, the method further includes a step of condensing the volatilized beta-lactone from the separating step.

In some embodiments, the method further includes adding a portion of the beta-lactone stream to the feed stream. In some embodiments, the beta-lactone stream is added to the feed until the weight percent of beta-lactone in the reaction product stream is in the range of about 10% to about 90%, then withdrawing a portion of the beta-lactone stream as a product to maintain the weight percent of beta-lactone in the reaction product stream in the range of about 10% to about 90%. In some embodiments, the beta-lactone stream is added to the feed until the weight percent of beta-lactone in the reaction product stream is in the range of about 30% to about 65%, then withdrawing a portion of the beta-lactone stream as a product to maintain the weight percent of beta-lactone in the reaction product stream in the range of about 30% to about 65%. In some embodiments, the beta-lactone stream is added to the feed until the weight percent of beta-lactone in the reaction product stream is in the range of about 43% to about 53%, then withdrawing a portion of the beta-lactone stream as a product to maintain the weight percent of beta-lactone in the reaction product stream in the range of about 43% to about 53%.

In some embodiments, the method further includes adding a second solvent to the beta lactone prior to the step of further treating the beta-lactone stream under conditions to convert the beta lactone.

In some embodiments, the step of further treating the beta-lactone stream under conditions to convert the beta lactone is performed in the gas phase.

In some embodiments, the boiling point of the solvent is at least 20° C. higher than the boiling point of the beta lactone. In some embodiments, the boiling point of the solvent is between about 20 and about 80° C. higher than the boiling point of the beta-lactone. In some embodiments, the boiling point of the solvent is about 30 to about 60° C. higher than the boiling point of the beta lactone.

In some embodiments, the epoxide has the formula

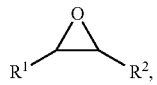

(I)

where, $R^1$ and $R^2$, are each independently selected from the group consisting of: —H; optionally substituted $C_{1-6}$ aliphatic; phenyl; optionally substituted $C_{1-6}$ heteroaliphatic; optionally substituted 3- to 6-membered carbocycle; and optionally substituted 3- to 6-membered heterocycle, and where $R^1$ and $R^2$ can optionally be taken together with intervening atoms to form an optionally substituted ring optionally containing one or more heteroatoms.

In some embodiments, the epoxide is chosen from the group consisting of: ethylene oxide; propylene oxide; 1,2-butylene oxide; 2,3-butylene oxide; epichlorohydrin; cyclohexene oxide; cyclopentene oxide; 3,3,3-Trifluoro-1,2-epoxypropane, styrene oxide; a glycidyl ether; and a glycidyl ester. In some embodiments, the epoxide is ethylene oxide. In some embodiments, the epoxide is propylene oxide.

In some embodiments, the step of further treating the beta-lactone stream under conditions to convert the beta lactone is performed in the presence of a compound selected from the group consisting of: an alcohol, an amine and a thiol, under conditions that produce the corresponding acrylic ester, acrylamide, or a thioacrylate respectively.

In some embodiments, the step of further treating the beta-lactone stream under conditions to convert the beta lactone is performed in the presence of a compound of formula H—Y to afford an acrylate having the formula:

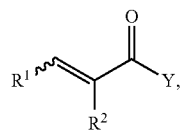

(II)

wherein, $R^1$ and $R^2$, are each independently selected from the group consisting of: —H, optionally substituted $C_{1-6}$ aliphatic, optionally substituted $C_{1-6}$ heteroaliphatic, optionally substituted 3- to 12-membered carbocycle, and optionally substituted 3- to 12-membered heterocycle, or $R^1$ and $R^2$ can optionally be taken together with intervening atoms to form an optionally substituted ring optionally containing one or more heteroatoms. In some embodiments, Y is selected from the group consisting of $OR^{13}$, $NR^{11}R^{12}$, and $SR^{13}$. In some embodiments, $R^{11}$, $R^{12}$, and $R^{13}$ are independently selected from the group consisting of: —H; optionally substituted $C_{1-32}$ aliphatic, optionally substituted $C_{1-32}$ heteroaliphatic, optionally substituted 3- to 14-membered carbocycle, and optionally substituted 3- to 14-membered heterocycle, or $R^{11}$ and $R^{12}$ can optionally be taken together with intervening atoms to form an optionally substituted ring optionally containing one or more heteroatoms.

In some embodiments, the feed stream comprises, ethylene oxide and a high boiling solvent that has a boiling point of at least 172° C. at atmospheric pressure; and the reaction product stream contains propiolactone.

In some embodiments, the feed stream comprises propylene oxide and a high boiling solvent that has a boiling point of at least 180° C. at atmospheric pressure; and the reaction product stream contains propiolactone.

In some embodiments, wherein the solvent is selected from the group consisting of: sulfolane; N-methyl pyrrolidone; 1,3-Dimethyl-2-imidazolidinone diglyme; triglyme; tetraglyme; ethylene carbonate; propylene carbonate; dibasic esters; THF, THF modified with a $C_{1-32}$ aliphatic; and mixtures of any two or more of these. In some embodiments, the solvent is THF. In some embodiments, the solvent is sulfolane. In some embodiments, the solvent is a dibasic ester. In some embodiments, the solvent is a mixture of sulfolane and THF. In some embodiments, the solvent is a mixture of sulfolane and THF modified with a $C_{1-32}$ aliphatic. In some embodiments, the solvent further comprises dimethyl ether isosorbide.

In some embodiments, the modified THF has the form:

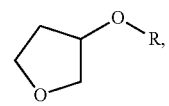

(IV)

wherein, R is an aliphatic, aromatic, ether, or ester group any of which contains more than four carbon atoms.

In some embodiments, the carbonylation catalyst comprises a metal carbonyl compound.

In some embodiments, the metal carbonyl compound has the general formula $[QM_y(CO)_w]^x$, where: Q is any ligand and need not be present; M is a metal atom; y is an integer from 1 to 6 inclusive; w is a number such as to provide the stable metal carbonyl; and x is an integer from −3 to +3 inclusive.

In some embodiments, M is selected from the group consisting of Ti, Cr, Mn, Fe, Ru, Co, Rh, Ni, Pd, Cu, Zn, Al, Ga and In. In some embodiments, wherein M is Co. In some embodiments, M is Co, y is 1, and w is 4.

In some embodiments, the carbonylation catalyst further comprises a Lewis acidic co-catalyst.

In some embodiments, the metal carbonyl compound is anionic, and the Lewis acidic co-catalyst is cationic. In some embodiments, the metal carbonyl complex comprises a carbonyl cobaltate and the Lewis acidic co-catalyst comprises a metal-centered cationic Lewis acid.

In some embodiments, the metal-centered cationic Lewis acid is a metal complex of formula $[M'(L)_b]^{c+}$, where, M' is a metal; each L is a ligand; b is an integer from 1 to 6 inclusive; c is 1, 2, or 3; and where, if more than one L is present, each L may be the same or different.

In some embodiments, is selected from the group consisting of: a transition metal, a group 13 or 14 metal, and a lanthanide. In some embodiments, M' is a transition metal or a group 13 metal. In some embodiments, M' is selected from the group consisting of aluminum, chromium, indium and gallium. In some embodiments, M' is aluminum. In some embodiments, M' is chromium.

In some embodiments, the Lewis acid includes a dianionic tetradentate ligand. In some embodiments, the dianionic tetradentate ligand is selected from the group consisting of: porphyrin derivatives; salen derivatives; dibenzotetramethyltetraaza[14]annulene ("TMTAA") derivatives; phthalocyaninate derivatives; and derivatives of the Trost ligand.

In some embodiments, the treating step is mediated by a catalyst. In some embodiments, the catalyst in the treating step is an acid catalyst. In some embodiments, the catalyst in the treating step is a basic catalyst.

In some embodiments, the reacting step is performed in adiabatic reactor. In some embodiments, the adiabatic reactor is a tubular reactor. In some embodiments, the adiabatic reactor is a shell and tube reactor.

In some embodiments, the reacting step is performed at a pressure from about 50 psi to about 5000 psi. In some embodiments, the reacting step is performed at a pressure from about 50 psi to about 1500 psi. In some embodiments, the reacting step is performed at a pressure from about 200 psi to about 800 psi. In some embodiments, the reacting step is performed at a pressure of about 400 psi.

In some embodiments, the reacting step is performed at a temperature from about 0° C. to about 125° C.

In some embodiments, the reacting step is performed at a temperature from about 30° C. to about 100° C. In some embodiments, the reacting step is performed at a temperature from about 40° C. to about 80° C.

In some embodiments, the carbon monoxide in the reacting step is supplied as an industrial gas stream comprising carbon monoxide and one or more additional gases. In some embodiments, the industrial gas stream comprises syngas. In some embodiments, the carbon monoxide in the reacting step is supplied in substantially pure form.

In some embodiments, the beta-lactone stream comprises residual unreacted epoxide, carbon monoxide, or solvent. In some embodiments, the epoxide, carbon monoxide or solvent are returned to the feed stream. In some embodiments, a portion of the beta-lactone stream is returned to the feed.

In various aspects the present invention provides a method including steps of reacting the contents of a feed stream comprising an epoxide, a solvent, a carbonylation catalyst and carbon monoxide to produce a reaction product stream comprising a beta-lactone; separating at least a portion of the beta-lactone in the reaction product stream from the solvent and carbonylation catalyst to produce: i) a beta-lactone stream comprising the beta-lactone, and ii) a catalyst recycling stream comprising the carbonylation catalyst; and adding the catalyst recycling stream to the feed stream.

In some embodiments, the separating step includes steps of a first separating step to separate the reaction product stream into i) a gaseous stream comprising carbon monoxide, and the epoxide; and ii) a liquid stream comprising the beta-lactone, and the carbonylation catalyst; and a second separating step to separate at least a portion of the beta-lactone in the liquid stream from the solvent and carbonylation catalyst to produce: i) a beta-lactone stream comprising the beta-lactone; and ii) the catalyst recycling stream comprising the carbonylation catalyst.

In some embodiments, the first separating step includes steps of separating the reaction product stream into i) a gaseous stream comprising carbon monoxide and a portion of the epoxide, and ii) a liquid stream comprising a remainder of the epoxide, the beta-lactone, and the carbonylation catalyst; and separating the liquid stream into i) an epoxide stream comprising the remainder of the epoxide; and ii) the nonvolatile stream comprising the beta-lactone, and the carbonylation catalyst.

In some embodiments, the catalyst recycling stream further includes at least a portion of the solvent, where the solvent has a boiling point higher than the boiling point of the beta-lactone. In some embodiments, the method includes the step of returning the gaseous stream to the feed stream.

In some embodiments, the method includes the step of returning the beta-lactone stream to the feed stream. In some embodiments, the method includes the step of returning the catalyst recycling stream to the feed stream.

In some embodiments, the gaseous stream further includes a portion of the solvent, where the solvent has a boiling point lower than the boiling point of the beta-lactone. In some embodiments, the gaseous stream is returned to the feed stream. In some embodiments, the method includes the step of returning at least one of the gaseous stream and the epoxide stream to the feed stream. In some embodiments, the method includes the step of returning the liquid stream to the feed stream. In some embodiments, the method includes the step of returning the nonvolatile stream to the feed stream. In some embodiments, the epoxide stream further comprises a portion of the solvent, where the solvent has the boiling point lower than the boiling point of the beta-lactone. In some embodiments, the gaseous stream is returned to the feed stream.

In some embodiments, the feed stream further comprises a Lewis base additive. In some embodiments, the Lewis base additive is selected from modified THF; 2,6-lutidine; imidazole; 1-methylimidazole 4-dimethylaminopyridine; trihexylamine, and triphenylphosphine.

In various aspects, the invention includes a method including steps of: reacting the contents of a feed stream comprising an epoxide, a solvent with a carbonylation catalyst and carbon monoxide to produce a reaction product stream comprising a beta-lactone; returning the entirety of the reaction product stream to the feed stream until the weight percent of beta-lactone in the reaction product stream is in a predetermined range; then separating at least a portion of the beta-lactone in the reaction product stream from the solvent and carbonylation catalyst to produce: i) a beta-lactone stream comprising the beta-lactone, and ii) a catalyst recycling stream comprising the carbonylation catalyst and the solvent; and adding the catalyst recycling stream to the feed stream.

In some embodiments, the reaction product stream is returned to the feed until the weight percent of beta-lactone in the reaction product stream is in the range of about 10% to about 90%, then withdrawing a portion of the beta-lactone stream as a product to maintain the weight percent of beta-lactone in the reaction product stream in the range of about 10% to about 90%, is in the range of about 30% to about 65%, or in the range of about 43% to about 53%.

DETAILED DESCRIPTION OF VARIOUS EMBODIMENTS OF THE INVENTION

Figure 1:
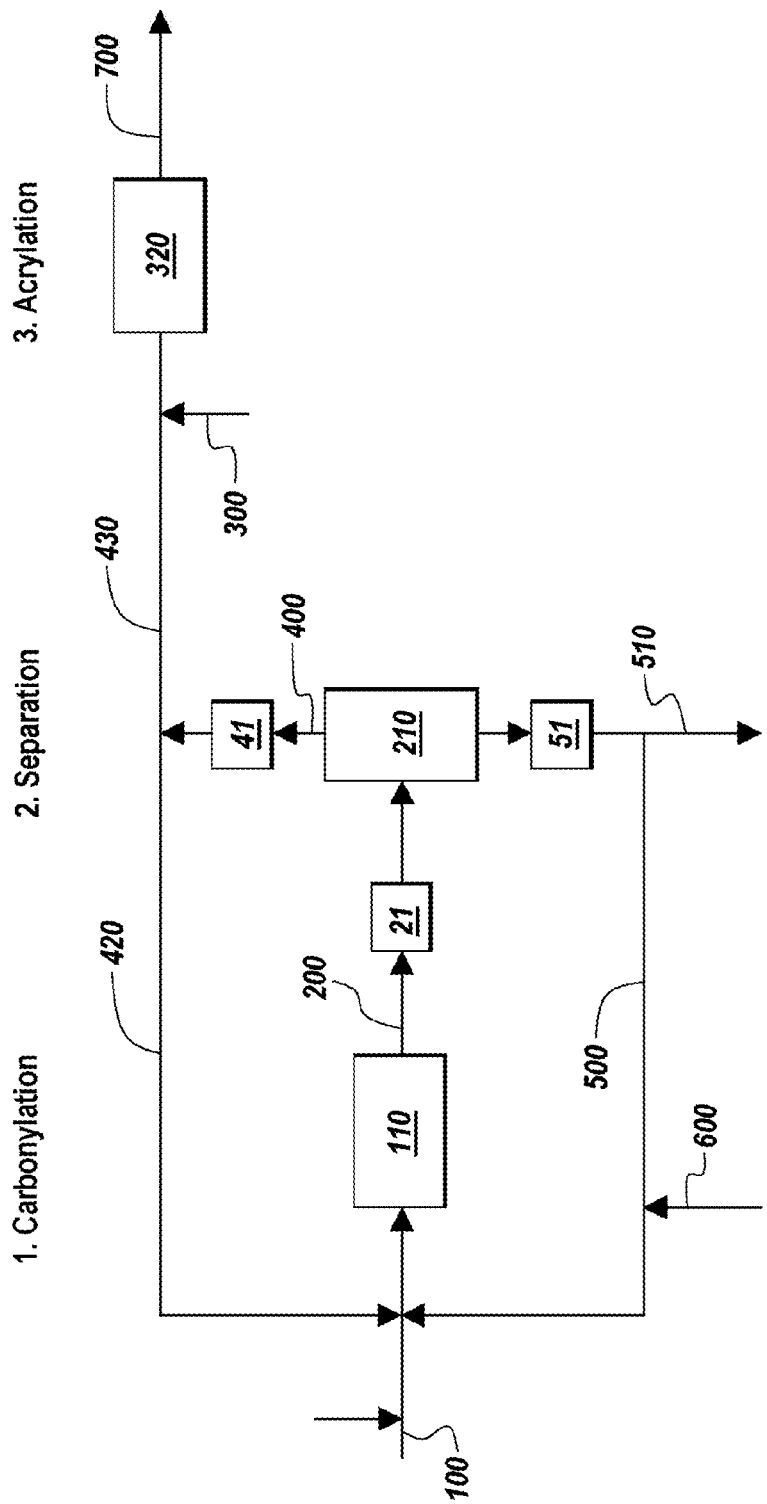
FIG. 1 shows a process flow diagram of exemplary reaction system.
Figure 2:
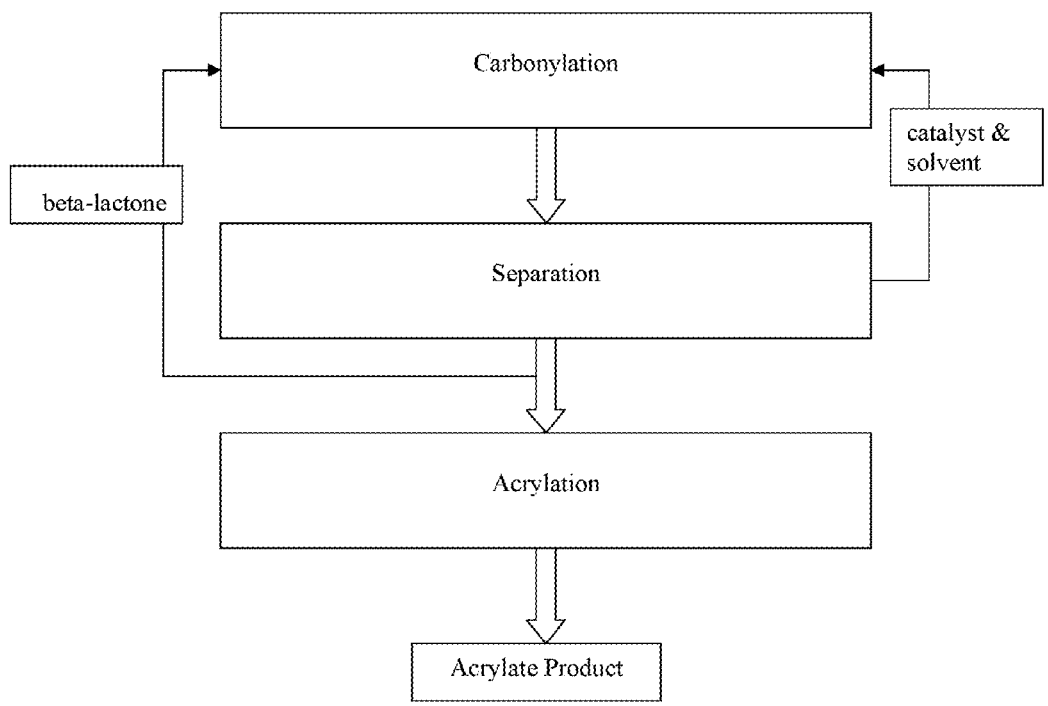
FIG. 2 shows a flow chart of exemplary reaction and process steps.

The present invention encompasses methods for the-continuous production of beta-lactone from an epoxide feedstock. In various aspects, the invention encompasses methods of carbonylation 1 of epoxide compounds (e.g., ethylene oxide) to yield a beta-lactone (e.g., beta-propiolactone) in a reaction product stream 200. The beta-lactone is further separated 2 or isolated from the other components of the reaction product stream. The beta-lactone is further transformed to an acrylate (e.g., acrylic acid) 3. In some embodiments, the carbonylation reaction 1 is in the presence a catalyst. In some embodiments, the epoxide is reacted with carbon monoxide. In some embodiments, the catalyst is present in a solvent. Scheme 1 below illustrates the reaction sequence in one embodiment of the invention.

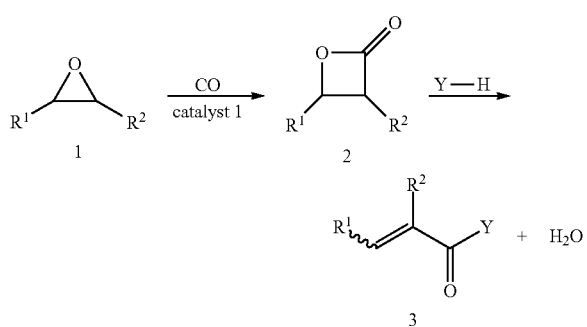

Definitions

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5$^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, 3$^{rd}$ Edition, Cambridge University Press, Cambridge, 1987; the entire contents of each of which are incorporated herein by reference.

Certain compounds, as described herein may have one or more double bonds that can exist as either a Z or E isomer, unless otherwise indicated. The invention additionally encompasses the compounds as individual isomers substantially free of other isomers and alternatively, as mixtures of various isomers, e.g., racemic mixtures of enantiomers. In addition to the above-mentioned compounds per se, this invention also encompasses compositions comprising one or more compounds.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, a compound may, in some embodiments, be provided substantially free of one or more corresponding stereoisomers, and may also be referred to as "stereochemically enriched."

The terms "halo" and "halogen" as used herein refer to an atom selected from fluorine (fluoro, —F), chlorine (chloro, —Cl), bromine (bromo, —Br), and iodine (iodo, —I). The term "halogenic" as used herein refers to a compound substituted with one or more halogen atoms.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In certain embodiments, aliphatic groups contain 1-12 carbon atoms. In certain embodiments, aliphatic groups contain 1-8 carbon atoms. In certain embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In certain embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups.

The term "epoxide", as used herein, refers to a substituted or unsubstituted oxirane. Substituted oxiranes include monosubstituted oxiranes, disubstituted oxiranes, trisubstituted oxiranes, and tetrasubstituted oxiranes. Such epoxides may be further optionally substituted as defined herein. In certain embodiments, epoxides comprise a single oxirane moiety. In certain embodiments, epoxides comprise two or more oxirane moieties.

The term "acrylate" or "acrylates" as used herein refer to any acyl group having a vinyl group adjacent to the acyl carbonyl. The terms encompass mono-, di- and tri-substituted vinyl groups. Examples of acrylates include, but are not limited to: acrylate, methacrylate, ethacrylate, cinnamate (3-phenylacrylate), crotonate, tiglate, and senecioate. Because it is known that cylcopropane groups can in certain instances behave very much like double bonds, cyclopropane esters are specifically included within the definition of acrylate herein.

The term "polymer", as used herein, refers to a molecule of high relative molecular mass, the structure of which comprises the multiple repetition of units derived, actually or conceptually, from molecules of low relative molecular mass. In certain embodiments, a polymer is comprised of only one monomer species (e.g., polyethylene oxide). In certain embodiments, a polymer of the present invention is a copolymer, terpolymer, heteropolymer, block copolymer, or tapered heteropolymer of one or more epoxides.

The term "unsaturated", as used herein, means that a moiety has one or more double or triple bonds.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. The terms "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic. In certain embodiments, the terms "3- to 14-membered carbocycle" and "$C_{3-14}$ carbocycle" refer to a 3- to 8-membered saturated or partially unsaturated monocyclic carbocyclic ring, or a 7- to 14-membered saturated or partially unsaturated polycyclic carbocyclic ring.

Representative carbocyles include cyclopropane, cyclobutane, cyclopentane, cyclohexane, bicyclo[2,2,1]heptane, norbornene, phenyl, cyclohexene, naphthalene, spiro [4.5]decane, The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like. In certain embodiments, the terms "6- to 10-membered aryl" and "$C_{6-10}$ aryl" refer to a phenyl or an 8- to 10-membered polycyclic aryl ring.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14 electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. In certain embodiments, the term "5- to 14-membered heteroaryl" refers to a 5- to 6-membered heteroaryl ring having 1 to 3 heteroatoms independently selected from nitrogen, oxygen, or sulfur, or an 8- to 14-membered polycyclic heteroaryl ring having 1 to 4 heteroatoms independently selected from nitrogen, oxygen, or sulfur.

As used herein, the terms "heterocycle", "heterocyclyl", "heterocyclic radical", and "heterocyclic ring" are used interchangeably and refer to a stable 5- to 7-membered monocyclic or 7-14-membered bicyclic heterocyclic moiety that is either saturated, partially unsaturated, or aromatic and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). In some embodiments, the term "3- to 14-membered heterocycle" refers to a 3- to 8-membered saturated or partially unsaturated monocyclic heterocyclic ring having 1 to 2 heteroatoms independently selected from nitrogen, oxygen, or sulfur, or a 7- to 14-membered saturated or partially unsaturated polycyclic heterocyclic ring having 1-3 heteroatoms independently selected from nitrogen, oxygen, or sulfur.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)N(R°)$_2$; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°)$_2$, wherein each R°may be substituted as defined below and is independently hydrogen, C$_{1-8}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or polycyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-4}$C(O)N(R°)$_2$; —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of Rt are independently halogen, —R$^\bullet$, —(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "catalyst" refers to a substance the presence of which increases the rate of a chemical reaction, while not being consumed or undergoing a permanent chemical change itself.

Carbonylation

The carbonylation step is performed contacting a feed stream 100 comprising epoxide, and a carbonylation catalyst with carbon monoxide to provide a reaction product stream 200 containing a carbonylation product formed from the epoxide.

Reactants

Turning first to the carbonylation reaction, the reactants may include various epoxides, including ethylene oxide, propylene oxide.

In certain embodiments, the epoxide starting material has formula I

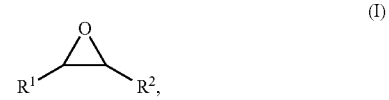
(I)

where, R$^1$ and R$^2$ are each independently selected from the group consisting of: —H; optionally substituted C$_{1-6}$ aliphatic; optionally substituted phenyl; optionally substituted C$_{1-6}$ heteroaliphatic; optionally substituted 3- to 6-membered carbocycle; and optionally substituted 3- to 6-membered heterocycle, where R$^1$ and R$^2$ can optionally be taken together with intervening atoms to form a 3- to 10-membered, substituted or unsubstituted ring optionally containing one or more heteroatoms.

In some embodiments, R$^1$ is hydrogen. In some embodiments, R$^1$ is phenyl. In some embodiments, R$^1$ is optionally substituted C$_{1-6}$ aliphatic. In some embodiments, R$^1$ is n-butyl. In some embodiments, R$^1$ is n-propyl. In some embodiments, R$^1$ is ethyl. In some embodiments, R$^1$ is —CF$_3$. In some embodiments, R$^1$ is —CH$_2$Cl. In other embodiments, R$^1$ is methyl.

In some embodiments, R$^2$ is hydrogen. In some embodiments, R$^2$ is optionally substituted C$_{1-6}$ aliphatic. In some embodiments, R$^2$ is methyl.

In certain embodiments, R$^1$ and R$^2$ are taken together with intervening atoms to form a 3- to 10-membered, substituted or unsubstituted ring optionally containing one or more heteroatoms. In some embodiments, R$^1$ and R$^2$ are taken together with intervening atoms to form a cyclopentyl or cyclohexyl ring.

In certain embodiments, an epoxide is chosen from the group consisting of: ethylene oxide, propylene oxide, 1,2-butylene oxide, 2,3-butylene oxide, epichlorohydrin, cyclohexene oxide, cyclopentene oxide, 3,3,3-Trifluoro-1,2-epoxypropane, styrene oxide, a glycidyl ether, and a glycidyl ester.

In certain embodiments, the epoxide is ethylene oxide.

In certain embodiments, the epoxide is propylene oxide.

In certain embodiments, the carbonylation step comprises the reaction shown in Scheme 2:

Scheme 2

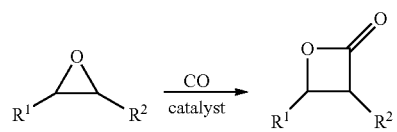

where, each of R$^1$ and R$^2$ is as defined above and described in classes and subclasses herein.

In certain embodiments, the carbonylation step comprises the reaction shown in Scheme 3:

Scheme 3

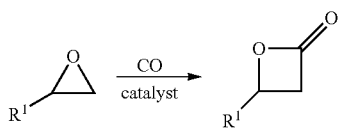

where, $R^1$ is selected from the group consisting of —H and $C_{1-6}$ aliphatic.

In certain embodiments, the carbonylation step comprises the reaction shown in Scheme 4:

Scheme 4

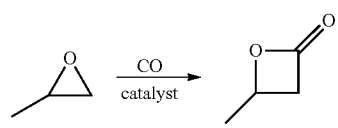

In certain embodiments, the carbonylation step comprises the reaction shown in Scheme 5:

Scheme 5

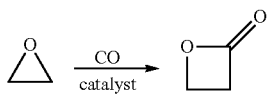

Additional reactants can include carbon monoxide, or a mixture of carbon monoxide and another gas. In some embodiments, carbon monoxide is provided in a mixture with hydrogen (e.g., Syngas). The ratio of carbon monoxide and hydrogen can be any ratio, including by not limited to 1:1, 1:2, 1:4, 1:10, 10:1, 4:1, or 2:1. In some embodiments, the carbon monoxide is provided in mixture with gases as an industrial process gas. The carbon monoxide sources include but are not limited to: wood gas, producer gas, coal gas, town gas, manufactured gas, hygas, Dowson gas or water gas, among others. In some embodiments, the carbon monoxide is provided at super-atmospheric pressure. The quantity of carbon monoxide should be supplied to effect efficient conversion of the epoxide starting material to a beta-lactone.

Catalyst

In certain embodiments, a carbonylation catalyst comprises a metal carbonyl complex. In some embodiments, a metal carbonyl complex has the general formula $[QM_y(CO)_w]^x$, where:

Q is any ligand and need not be present;
M is a metal atom;
y is an integer from 1 to 6 inclusive;
w is a number such as to provide the stable metal carbonyl; and
x is an integer from −3 to +3 inclusive.

In certain embodiments where a metal carbonyl complex has the formula $[QM_y(CO)_w]^x$, M is selected from the group consisting of Ti, Cr, Mn, Fe, Ru, Co, Rh, Ni, Pd, Cu, Zn, Al, Ga and In. In certain embodiments, M is Co. In certain embodiments, a metal carbonyl complex is $Co(CO)_4^-$.

In certain embodiments, a carbonylation catalyst further comprises a Lewis acidic component. In certain embodiments, a Lewis acidic component is cationic. In some embodiments, a carbonylation catalyst comprises an anionic metal carbonyl complex (e.g. x is a negative integer) and a cationic Lewis acidic component. In certain embodiments, the metal carbonyl complex comprises a carbonyl cobaltate and the Lewis acidic component comprises a metal-centered cationic Lewis acid.

In certain embodiments, a metal-centered cationic Lewis acid is a metal complex of formula $[M'(L)_b]^{c+}$, where:

M' is a metal;
each L is a ligand;
b is an integer from 1 to 6 inclusive;
c is 1, 2, or 3; and
where, if more than one L is present, each L may be the same or different.

In some embodiments where a metal-centered Lewis acid is a metal complex of formula $[M'(L)_b]^{c+}$, M' is selected from the group consisting of: a transition metal, a group 13 or 14 metal, and a lanthanide. In certain embodiments, M' is a transition metal or a group 13 metal. In certain embodiments, is selected from the group consisting of aluminum, chromium, indium and gallium. In certain embodiments, M' is aluminum. In certain embodiments, M' is chromium.

In certain embodiments, a metal-centered Lewis-acidic component of a carbonylation catalyst includes a dianionic tetradentate ligand. In certain embodiments, a dianionic tetradentate ligand is selected from the group consisting of: porphyrin derivatives, salen derivatives, dibenzotetramethyltetraaza[14]annulene ("TMTAA") derivatives, phthalocyaninate derivatives, and derivatives of the Trost ligand.

In some embodiments, a dianionic tetradentate ligand is ClTPP (meso-tetra(4-chlorophenyl)porphyrin). In some embodiments, a dianionic tetradentate ligand is TPP (tetraphenylporphyrin). In some embodiments, a dianionic tetradentate ligand is a salen (N,N'-ethylenebis(salicylimine) ligand. In some embodiments, a dianionic tetradentate ligand is a salph (N,N'-bis(salicylidene)-o-phenylenediamine) ligand. In some embodiments, a dianionic tetradentate ligand is a salcy (N,N'-bis(3,5-di-tert-butylsalicylidene)-1,2-diaminocyclohexane) ligand.

In certain embodiments, a carbonylation catalyst comprises a carbonyl cobaltate in combination with an aluminum porphyrin compound as a Lewis-acidic component. In some embodiments, a carbonylation catalyst comprises $[(TPP)Al][Co(CO)_4]$. In some embodiments, a carbonylation catalyst comprises $[(ClTPP)Al][Co(CO)_4]$.

In certain embodiments, a carbonylation catalyst comprises a carbonyl cobaltate in combination with a chromium porphyrin compound as a Lewis-acidic component. In some embodiments, a carbonylation catalyst comprises $[(TPP)Cr][Co(CO)_4]$. In some embodiments, a carbonylation catalyst comprises $[(ClTPP)Cr][Co(CO)_4]$.

In certain embodiments, a carbonylation catalyst comprises a carbonyl cobaltate in combination with a chromium salen compound as a Lewis-acidic component. In some embodiments, a carbonylation catalyst comprises $[(salcy)Cr][Co(CO)_4]$.

In certain embodiments, a carbonylation catalyst comprises a carbonyl cobaltate in combination with a chromium salophen compound as a Lewis-acidic component. In some embodiments, a carbonylation catalyst comprises $[(salph)Cr][Co(CO)_4]$.

In certain embodiments, a carbonylation catalyst comprises a carbonyl cobaltate in combination with an aluminum salen compound as a Lewis-acidic component. In certain embodiments, a carbonylation catalyst comprises a carbonyl cobaltate in combination with an aluminum salophen compound as a Lewis-acidic component. In some embodiments, a carbonylation catalyst comprises [(salph)Al][Co(CO)$_4$].

In certain embodiments, a carbonylation catalyst further comprises one or more electron donating groups. In certain embodiments, such electron donating groups are solvent molecules. In some embodiments, an electron donating group is a solvent molecule in which the catalyst, or a portion thereof, was synthesized. In certain embodiments, an electron donating group is THF.

Solvents

In some embodiments, the carbonylation catalyst is present in a solvent. The solvent may be selected from any solvent, and mixtures of solvents. Additionally, beta-lactone may be utilized as a co-solvent. Solvents for the catalyst include, but are not limited to, tetrahydrofuran ("THF"), sulfolane, N-methyl pyrrolidone, 1,3 dimethyl-2-imidazolidinone, diglyme, triglyme, tetraglyme, diethylene glycol dibutyl ether, ethylene carbonate, propylene carbonate, butylene carbonate, dibasic esters, diethyl ether, acetonitrile, ethyl acetate, dimethoxy ethane, acetone, dioxane, THF modified with a $C_{1-32}$ alphatic chain. In general, aprotic solvents are suitable for the carbonylation reaction step. In some embodiments, the modified THF has the form:

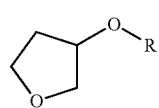

(VI)

wherein, R is an aliphatic, aromatic, ether, or ester group any of which contains more than four carbon atoms. In some embodiments, the modified THF has the formula:

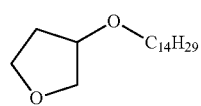

(VII)

In some embodiments, the solvent includes a catalyst stabilizer. Various catalyst stabilizers include, but are not limited to isosorbide ethers such as isosorbide dimethylether.

In some embodiments, the feed stream 100 includes a Lewis base additive. In some embodiments, such Lewis base additives can stabilize or reduce deactivation of the catalysts. In some embodiments, the Lewis base additive is a modified THF; 2,6-lutidine; imidazole, 1-methylimidazole 4-dimethylaminopyridine, trihexylamine and triphenylphosphine.

In some embodiments, solvents suitable for the process have a boiling point higher than that of the beta-lactone produced by the carbonylation reaction. For example, in the carbonylation of ethylene oxide, the high boiling point solvent has a boiling point higher than about 108° C. at 50 Torr since the beta-lactone produced (beta-propiolactone) has a boiling point of 108° C. at that pressure. For propylene oxide, the corresponding beta-lactone (beta-butyrolactone) has a boiling point of 86-87° C. at 50 Torr, and the high boiling solvent should have a higher boiling point than that.

In some embodiments, the solvent, or a mixture of solvents, is selected to facilitate separation 2 of the beta-lactone from the reaction product stream. Generally, the separation is effected based on boiling point differential between the solvent and the beta-lactone. In some embodiments, the boiling point of the solvent is higher than the boiling of the beta-lactone, when compared at the same pressure. In some embodiments, the boiling point of the solvent is at least about 20 degrees Celsius higher than the boiling point of the beta-lactone when compared at the same pressure. In some embodiments, the boiling point of the solvent is at least about 30 degrees Celsius higher than the boiling point of the beta-lactone when compared at the same pressure. In some embodiments, the boiling point of the solvent is at least about 40 degrees Celsius higher than the boiling point of the beta-lactone when compared at the same pressure. In some embodiments, the boiling point of the solvent is at least about 50 degrees Celsius higher than the boiling point of the beta-lactone when compared at the same pressure.

In some embodiments, the solvent has a boiling point that is lower than the boiling point of the beta-lactone when compared at the same pressure. In certain embodiments, the boiling point of the solvent is selected to be between about 30° C. and about 130° C. at atmospheric pressure. In certain embodiments, the boiling point of the solvent is selected to be between about 30 and about 100° C. at atmospheric pressure. In some embodiments, the boiling point of the solvent is at least 10 degrees lower than the boiling point of the beta-lactone when compared at the same pressure. In some embodiments, the boiling point of the solvent is at least 20 degrees lower than the boiling of the beta-lactone when compared at the same pressure. In some embodiments, the boiling point of the solvent is at least 30 degrees lower than the boiling of the beta-lactone when compared at the same pressure. In some embodiments, the boiling point of the solvent is at least 40 degrees lower than the boiling point of the beta-lactone when compared at the same pressure. In some embodiments, the boiling point of the solvent is at least 50 degrees lower than the boiling of the beta-lactone when compared at the same pressure. In some embodiments, the solvent is comprised of a mixture of solvents one of which may have boiling point higher than the boiling of the beta-lactone, and the other solvent may have a boiling point lower than the boiling point of the beta-lactone.

In some embodiments, the reactants are completely soluble in the solvent under the reaction conditions. Additionally, the catalyst may be soluble in the solvent under the reaction conditions. In some embodiments, the reactants or catalyst are only partially, or insoluble in the solvent under the reaction conditions. In some embodiments, only the catalyst is soluble in the solvent.

In some embodiments, the solvent is provided "fresh." In some embodiments, the solvent is recycled after the separation step. Solvent recycling may include the addition of fresh solvent to the recycle stream.

In some embodiments, the solvent includes beta-lactone. In general, the use of a beta-lactone as a co-solvent aides in eventual separation of the beta-lactone product from the non-beta-lactone solvent, if present. The separation of the beta-lactone from the remainder of the reaction product stream 200 becomes easier as the concentration of beta-lactone in reaction product stream increases.

Carbonylation Reaction Conditions

The carbonylation reaction conditions are selected based on a number of factors to effect conversion of the epoxide to a beta-lactone. Temperature, pressure, and reaction time influence reaction speed and efficiency. Additionally the ratio of reactants to each other and to the catalyst effect reaction speed and efficiency.

In some embodiments, the reaction temperature can range from between about −20° C., to about 600° C. In some embodiments, the reaction temperature is about −20° C., about 0° C., about 20° C., about 40° C., about 60° C., about 80° C., about 100° C., about 200° C., about 300° C., about 400° C., about 500° C. or about , about 600° C. In some embodiments, the temperature is in a range between about 40° C. and about 120° C. In some embodiments, the temperature is in a range between about 40° C. and about 80° C. In some embodiments, the temperature is in a range between about 50° C. and about 70° C. In some embodiments, the reactants, catalyst and solvent are supplied to the reactor at standard temperature, and then heated in the reactor. In some embodiments, the reactants are pre-heated before entering the reactor.

In some embodiments, the reaction pressure can range from between about 50 psig to about 5000 psig. In some embodiments, the reaction pressure is about 100 psig, about 200 psig, about 300 psig, about 400 psig, about 500 psig, about 600 psig, about 700 psig, about 800 psig, about 900 psig, or about 1000 psig. In some embodiments, the pressure ranges from about 50 psig to about 2000 psig. In some embodiments, the pressure ranges from about 100 psig to 1000 psig. In some embodiments, the pressure ranges from about 200 psig to about 800 psig. In some embodiments, the reaction pressure is supplied entirely by the carbon monoxide. For example, the reactants, catalyst and solvent are charged to the reactor at atmospheric pressure, or under a vacuum, and carbon monoxide is added to the reactor to increase pressure to the reaction pressure. In some embodiments, all reactants, solvent and catalyst are supplied to the reactor at reaction pressure.

In some embodiments, the ratio of catalyst to epoxide is selected, based on other reaction conditions, so that the reaction proceeds in an economical and time-feasible manner. In some embodiments, the ratio of catalyst to epoxide is about 1:10000 on a molar basis. In some embodiments, the molar ratio of catalyst to epoxide is about 1:5000, is about 1:2500, is about 1:2000, is about 1:1500, is about 1:1000, is about 1:750, is about 1:500, is about 1:250, is about 1: 200, is about 1: 150, or is about 1:100. In some embodiments, the concentration of the epoxide is in the range between about 0.1 M and about 5.0 M. In some embodiments, the concentration of the epoxide is in the range between about 0.5 M and about 3.0 M.

In some embodiments, the reaction is maintained for a period of time sufficient to allow complete, near complete reaction of the epoxide to beta-lactone or as complete as possible based on the reaction kinetics and or reaction conditions. In some embodiments, the reaction time is maintained for about 12 hours, about 8 hours, about 6 hours, about 3 hours, about 2 hours or about 1 hour. In some embodiments, the reaction time is established as a residence time within the reactor 110. The reaction can be halted by reducing the reactor temperature or pressure, withdrawing a particular reactant or introducing a quenching compound. The reaction may be halted at any point or any percentage conversion of epoxide to beta-lactone. E.g., the reaction may be halted when 50% of the epoxide is converted to beta-lactone.

Carbonylation Reaction Products

As described above, the primary reaction product of the carbonylation reaction is a beta-lactone. Additionally, the reaction product stream 200 may contain other reaction by-products, un-reacted reactants, as well as catalyst and solvent. In some embodiments, the un-reacted reactants include epoxide or carbon monoxide. As such, the reaction may not proceed to completion and may be considered a partial reaction.

In some embodiments, the amount of un-reacted epoxide is sufficient to prevent the formation of a succinic anhydride, a carbonylation reaction byproduct. Without being bound by a particular theory, it is speculated that the second reaction converting the beta-lactone to succinic anhydride does not proceed, unless substantially all of the epoxide is consumed. Thus a remaining portion of the epoxide feed to the reactor that exits un-reacted appears to prevent the formation of succinic anhydride. In some embodiments, the reaction product stream 200 contains unconverted epoxide in an amount of at least about 5% epoxide, at least about 3% epoxide, at least about 1% epoxide or at least about 0.1%, by weight. In some embodiments, the reaction is performed in a continuous flow format and epoxide is added at a rate sufficient to maintain the concentration in the above-described levels. In certain embodiments where the reaction is performed in a reactor where the reaction conditions vary over the volume of the reactor, the epoxide feed is chosen to maintain the lowest epoxide concentration in the reactor above the concentrations described above.

In some embodiments, by-product formation includes the formation of anhydride having the formula:

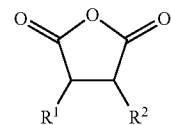

where $R^1$ and $R^2$ correspond to the same groups in the epoxide feedstock. In some embodiments, by-product formation includes the formation of one or more of the following compounds: crotonaldehyde, acrylic acid, 1,4 dioxane, acrylic acid dimers and trimers, 2-hydroxyethyl acrylate, 2,5 hexandienal, 3-oxacaprolactone, diethylene glycol monoacrylate, 3-hydroxypropionic acid, diethylene glycol diacrylate, 5-valeroactone and/or 2,6-dimethyl-1,3-dioxan-4-ol.

Reaction Mode

In some embodiments, the carbonylation reaction 1 is performed in a continuous operation. The reactants are continuously fed to a reactor 110. In some embodiments, the reactor 110 is stirred. In some embodiments, there is no stirring in the reactor 110, in some embodiments, reactor 110 incorporates one or more static mixers. In some embodiments, the reactor 110 includes a gas-entrainment impeller. The reactants may be fed to the reactor 110 at standard temperature and pressure and then heated or pressurized to reaction conditions once in the reactor 110. The reactor 110 itself may be any reactor conducive to continuous operation, including by not limited to a continuously stirred tank reactor or a tubular reactor. In some embodiments, the reactor 110 is an adiabatic reactor, and/or an isothermal reactor. In some embodiments, the reactor pressure is constant. In some embodiments, the reactor pressure varies as the reaction progresses. In some embodiments, the reactor temperature varies as the reaction progress. In some embodiments, the reaction is performed in a batch operation. One of ordinary skill in the art will recognize the temperatures, pressures, catalyst ratios, concentrations of reactants, catalyst and solvents, flow rates can all be optimized or varied to achieve a given reaction outcome.

In some embodiments, as described above, the various individual reaction products, or even the entire reaction product stream 200 can be recycled to the carbonylation reactor 110 or the feed stream 100 as a recycle. In some embodiments, the reaction products are separated in to at least two streams, as described below. Generally, at least one stream will contain at least the solvent and catalyst and the other stream will contain at least the beta-lactone product. Either or both of these streams may be recycled to the outset of the carbonylation reaction. In some embodiments, one stream will contain solvent and the other will contain the remainder of the reaction product stream 200.

In some embodiments, the catalyst and/or solvent stream is recycled to the feed stream or to the carbonylation reactor. In some embodiments, the portion of the solvent and/or catalyst from the reaction product stream 200 recycled to the carbonylation reactor 110 or feed stream 100 ranges from about 0% to about 100%. In some embodiments, the portion of the solvent and/or catalyst from the reaction product stream 200 recycled to the carbonylation reactor 110 or feed stream 100 is about 100%, about 90%, about 80%, about 70%, about 60%, about 50%, about 40%, about 30%, about 20%, about 10%, or about 0%. In some embodiments, a different percentage of the catalyst, as compared to the solvent is recycled, i.e., the proportions of either the catalyst or solvent component do not need to be equal.

In some embodiments, a portion of the catalyst and/or solvent is withdrawn from the recycling stream 500 as a waste 510. The portion of the catalyst and/or solvent withdrawn as waste 510, as compared to the total catalyst and/or solvent in the reaction product stream 200 may be in the range from about 0% to about 100%. The portion of the catalyst and/or solvent withdrawn as waste 510, as compared to the total catalyst and/or solvent in the reaction product stream 200 may be about 100%, about 90%, about 80%, about 70%, about 60, about 50%, about 40%, about 30%, about 20%, or about 10%.

In some embodiments, fresh catalyst and or solvent 600 is fed to either the recycling stream 500 or to the feed stream 100 in order to ensure that carbonylation reaction continues. The solvent and or catalyst added may make up for solvent and/or catalyst lost in the reaction, withdrawn as waste 510, or exhausted and no longer useful. The portion of the catalyst and/or solvent added, as compared to the total catalyst and/or solvent in the reaction product stream may be in the range from about 0% to about 100% of the flow rate of the stream. The portion of the catalyst and/or solvent added, as compared to the total catalyst and/or solvent in the reaction product stream 200 may be about 100%, about 90%, about 80%, about 70%, about 60, about 50%, about 40%, about 30%, about 20%, or about 10%.

In some embodiments, the beta-lactone is recycled to the carbonylation reactor 110 or the reactant feed stream 100. As discussed below the beta-lactone 400 is generally separated from the reaction product stream 200. In some embodiments, the portion of beta-lactone 420 from the reaction product stream 200 recycled to the carbonylation reactor or feed stream ranges from about 0% to about 100%. In some embodiments, the portion beta-lactone from the reaction product stream 200 recycled to the carbonylation reactor or feed stream is about 100%, about 90%, about 80%, about 70%, about 60%, about 50%, about 40%, about 30%, about 20%, about 10%, or about 0%. In some embodiments, 100% of the beta-lactone stream 400 is recycled to the reactor 110 or feed stream 100, until the percentage of beta-lactone in the reaction product stream 200 reaches a specified level. In some embodiments, the specified level ranges from about 5% to about 75%. In some embodiments, the level is about 5%, about 10%, about 20%, about 30%, about 40%, about 50%, about 60%, or about 75%.

The carbonylation step may begin without any beta-lactone present in the reaction product stream 200. After the start of the carbonylation, the beta-lactone produced from the carbonylation step may accumulate in the reaction product stream 200, and in some embodiments, no beta-lactone is separated from the reaction production stream 200 until the content of the beta-lactone in the reaction product stream 200 reaches a threshold value. In certain embodiments, the threshold value is from about 5 to about 10% by weight. In certain embodiments, the threshold value is from about 10% to about 20% by weight. In certain embodiments, the threshold value is from about 20% to about 30% by weight. In certain embodiments, the threshold value is from about 30% to about 40% by weight. In certain embodiments, the threshold value is from about 40% to about 50% by weight. In certain embodiments, the threshold value is from about 50% to about 60% by weight.

Separation

Another step in the process involves separating the reaction product stream 200 into at least two separate streams. At a minimum, the reaction product stream will be split into two separate streams, a beta-lactone stream 400 and a catalyst/solvent stream 500. The beta-lactone stream 400 will contain beta-lactone, but may also contain other compounds carried over from the product reaction stream 200, including epoxide, carbon monoxide, solvent, catalyst, and reaction by-products. Similarly, the catalyst/solvent stream 500 may contain primarily catalyst and solvent, but may also include other compounds carried over from the reaction product stream 200 including epoxide, carbon monoxide, beta-lactone, and reaction by-products.

In some embodiments, the separation is performed by exploiting the boiling point differential between the beta-lactone and the other components of the reaction product stream 200, primarily the catalyst and solvent. In some embodiments, the boiling point of the solvent is higher than the boiling point of the beta-lactone. In some embodiments, the beta-lactone is volatilized (e.g., evaporated) from the reaction product stream, leaving behind a mixture of catalyst, solvent and other compounds in the reaction product stream 200. In some embodiments, this includes exposing the reaction product stream 200 to reduced pressure. In some embodiments, this includes exposing reaction product stream 200 to increased temperature. In some embodiments, this includes exposing the reaction product stream 200 to both reduced pressure and increased temperature.

In some embodiments, the pressure is selected so that the boiling point of the beta-lactone is reduced by about 5° C. as compared to the boiling point at atmospheric pressure. In some embodiments, the pressure is selected so the boiling point of the beta-lactone is reduced by about 10° C. as compared to the boiling point at atmospheric pressure. In some embodiments, the pressure is selected so the boiling point of the beta-lactone is reduced by about 20° C. as compared to the boiling point at atmospheric pressure. In some embodiments, the pressure is selected so the boiling point of the beta-lactone is reduced by about 50° C. as compared to the boiling point at atmospheric pressure.

In some embodiments, the increased temperature is above the boiling point of the beta-lactone but below the boiling point of the solvent, at the selected pressure. In some embodiments, the temperature is at least about 20° C. below the boiling point of the solvent. In some embodiments, the temperature is at least about 30° C. below the boiling point of the solvent. In some embodiments, the temperature is at least about 50° C. below the boiling point of the solvent.

In some embodiments, the reduced pressure is in the range from about 1 Torr to about 760 Torr. In some embodiments, the pressure is in the range of about 1 Torr to about 400 Torr. In some embodiments, the pressure is in the range of about 5 Torr to about 200 Torr. In some embodiments, the pressure is in the range of about 10 Torr to about 100 Torr. In some embodiments, the pressure is in the range of about 20 Torr to about 50 Torr. In some embodiments, the pressure is about 50 Torr, about 100 Torr, about 150 Torr, about 200 Torr, about 250 Torr, about 300 Torr, about 400 Torr about 500 Torr, about 600 Torr or about 700 Torr.

In some embodiments, the separation step is performed at a pressure below about 100 Torr and at a temperature above about 120° C. In some embodiments, the separation step is performed at a pressure below about 50 Torr and at a temperature above about 100° C. In some embodiments, the separation step is performed at a pressure below about 50 Torr and at a temperature above about 50° C. In some embodiments, the separation step is performed at a pressure below about 50 Torr and at a temperature above about 110° C. In some embodiments, the separation step is performed at a pressure below about 50 Torr and at a temperature above about 90° C. In some embodiments, the separation step is performed at a pressure below about 20 Torr and at a temperature above about 60° C. In some embodiments, the separation step is performed at a pressure below about 10 Torr and at a temperature above about 50° C.

In some embodiments, the separation may be effected in a sequence of steps, each operating at an independent temperature and pressure. E.g., two steps may be used to obtain a more effective separation of beta-lactone, or a separate separation step may be used to isolate certain reaction by-products. In some embodiments, when a mixture of solvents is used multiple separation steps may required to remove particular solvents, individually or as a group, and effectively isolate the beta-lactone.

In certain embodiments, the separation of the beta-lactone from the reaction product stream 200 is performed in two stages. In some embodiments the process includes a preliminary separation step to remove one or more components of the product stream having boiling points below that of the beta-lactone product.

In some embodiments, the preliminary separation step includes separating the reaction product stream 200 into a gas stream comprising carbon monoxide, and unconverted epoxide; and a liquid stream comprising the beta-lactone, and the carbonylation catalyst. In the second step of separation, the liquid stream is further separated into a beta-lactone stream 400 comprising a portion of the beta-lactone; and a catalyst recycling stream 500 comprising a remainder of the beta-lactone and the carbonylation catalyst.

In some embodiments where one or more solvents with a boiling point lower than that of the beta-lactone are present, the lower boiling solvent may be volatilized (e.g., evaporated) from the reaction product stream in a preliminary separation step, leaving behind a mixture comprising catalyst, beta-lactone, other solvents (if any) and other compounds in the reaction product stream 200 which is then further treated to separate the beta-lactone stream.

In certain embodiments where the separation is performed in two stages, the first step of separation comprises exposing the reaction stream to mildly reduced pressure to produce the gas stream and the liquid stream. In certain embodiments where the separation is performed in two stages, the gas stream is returned to the carbonylation step.

In certain embodiments, the separation of the beta-lactone from the reaction product stream 200 is performed in three stages. In the first step of separation, the reaction product stream 200 is separated into a gaseous stream comprising carbon monoxide and a portion of the epoxide; and a liquid stream comprising a remainder of the epoxide, the beta-lactone, and the carbonylation catalyst. In the second step of separation, the liquid stream is separated into an epoxide stream comprising the remainder of the epoxide and, if present, any solvents with boiling points below that of the beta-lactone; and a second liquid stream comprising the beta-lactone, and the carbonylation catalyst. In the third step of separation, the second liquid stream is further separated into a beta-lactone stream 400 beta-lactone stream 400 comprising a portion of the beta-lactone; and a catalyst recycling stream 500 comprising a remainder of the beta-lactone and the carbonylation catalyst.

In certain embodiments where the separation is performed in three stages, the first step of separation comprises atmospheric venting of the reaction stream. In certain embodiments where the separation is performed in three stages, the second step of separation comprises exposing the liquid stream to mildly reduced pressure. In certain embodiments where the separation is performed in three stages, at least one of the gaseous stream and the epoxide stream is returned to the carbonylation step. In certain embodiments, the mildly reduced pressure is between about 100 Torr and 500 Torr. In certain embodiments, the mildly reduced pressure is between about 200 Torr and 400 Torr.

Lewis Base Additive

The feed stream may further comprise a Lewis base additive. The Lewis acidic component in the carbonylation catalyst may be coordinated to one of more Lewis base additives. The coordination of one or more Lewis base additives to the Lewis acidic component may stabilize the carbonylation catalyst during the carbonylation step and/or the separation step.

In some embodiments, the feed stream further comprises one or more Lewis base additives. In certain embodiments, a Lewis base additive is selected from nitrogen, phosphorous or oxygen Lewis bases. In certain embodiments, a Lewis base additive is selected from amines, phosphines, and ethers. In certain embodiments, a Lewis base additive is selected from the group consisting of: modified THF; 2,6-lutidine; imidazole; 1-methylimidazole and triphenylphosphine; 4-dimethylaminopyridine; trihexylamine.

Beta-lactone as Solvent

In some embodiments, the beta-lactone, the same chemical compound as the carbonylation product from an epoxide, may be used as the only solvent in the carbonylation reaction 1. In certain embodiments, the beta-lactone is used as a co-solvent and one or more additional solvents are present in the reaction 1. In certain embodiments, the boiling point of the other solvent present is greater than or less than the boiling point of the beta-lactone. In some embodiments, the beta-lactone is used as a co-solvent and one or more low-boiling point solvents are present in the process stream.

In some embodiments, where the methods of producing a beta-lactone from an epoxide comprise a carbonylation step 1 and a beta-lactone separation step 2, the beta-lactone is a co-solvent and one or more high-boiling point solvents are present in the process stream. The carbonylation step is performed by contacting a process stream comprising an epoxide, a beta-lactone, a high-boiling point solvent and a carbonylation catalyst with carbon monoxide to provide a reaction product stream 200 containing a carbonylation product from the epoxide, where the carbonylation product is the same chemical compound as the beta-lactone used as a co-solvent. The beta-lactone separation step 2 is performed by treating the reaction stream to conditions that cause volatilization of the beta-lactone to produce a beta-lactone stream 400 comprising a portion of the beta-lactone, and a catalyst recycling stream 500 comprising the carbonylation catalyst, the high-boiling point solvent, and a remainder of the beta-lactone.

In certain embodiments, where the beta-lactone is a co-solvent and one or more higher boiling solvents are present in the feed stream 100, the separation of the beta-lactone from the reaction product stream 200 is performed in two stages. In the first step of separation, the reaction product stream 200 is separated into a gas stream comprising carbon monoxide, and epoxide; and a liquid stream comprising beta-lactone, solvent, and carbonylation catalyst. In the second step of separation, the liquid stream is further separated into a beta-lactone stream 400 comprising a portion of the beta-lactone; and a catalyst recycling stream 500 comprising a remainder of the beta-lactone, the solvent, and the carbonylation catalyst. At least one of the beta-lactone stream 400 and the catalyst recycling stream 500 is returned to the first step of the process where it is recharged with additional epoxide and passed through the carbonylation reaction 1 again.

In certain embodiments, where the beta-lactone is a co-solvent and one or more lower boiling solvents are present in the feed stream 100, the separation of the beta-lactone from the reaction product stream 200 is performed in two stages. In the first step of separation, the reaction product stream 200 is separated into a gas stream comprising carbon monoxide, epoxide, and low boiling solvent; and a liquid stream comprising beta-lactone and carbonylation catalyst and higher boiling solvents if present. In the second step of separation, the liquid stream is further separated into a beta-lactone stream 400 comprising a portion of the beta-lactone; and a catalyst recycling stream 500 comprising a remainder of the beta-lactone, higher boiling solvent (if present), and the carbonylation catalyst. At least one of the beta-lactone stream 400 and the catalyst recycling stream 500 is returned to the first step of the process where it is recharged with additional epoxide and again passed through the carbonylation reaction 1.

In certain embodiments, where the beta-lactone is a co-solvent and one or more additional solvents are present in the process stream, the separation of the beta-lactone from the reaction mixture is performed in three stages. In the first step of separation, the reaction product stream 200 is separated into a gaseous stream comprising carbon monoxide and a portion of the epoxide; and a liquid stream comprising a remainder of the epoxide, the beta-lactone, the solvent, and the carbonylation catalyst. In the second step of separation, the liquid stream is separated into an epoxide stream comprising additional epoxide and lower boiling solvent (if present); and a second liquid stream comprising the beta-lactone, higher boiling solvent (if present), and the carbonylation catalyst. In the third step of separation, the second liquid stream is further separated into a beta-lactone stream 400 comprising a portion of the beta-lactone; and a catalyst recycling stream 500 comprising a remainder of the beta-lactone, higher boiling solvent (if present), and the carbonylation catalyst.

In some embodiments, the reaction product stream may be treated before the separation 2 is accomplished. Non-limiting examples of additional treatment 21 includes heating, cooling, decompressing, pressurizing, diluting, concentrating, degassing, filtering, purifying and any combination of these. Additionally, gaseous components of the reaction product stream (e.g., carbon monoxide, epoxide) may be vented from the reaction product stream 200 in conjunction with one or more treatments 21.

In some embodiments, the separation streams (e.g., the beta-lactone stream 400 and the catalyst solvent stream 500) are further treated before other operations. Non-limiting examples of additional treatment 41, 51 include heating, cooling, decompressing, pressurizing, diluting, concentrating, degassing, filtering, purifying, removing spent catalyst, removing reaction byproducts, adding fresh catalyst, adding one or more catalyst components, adding solvent, and any combination of these. Additionally, gaseous components of the beta-lactone stream 400 and the catalyst solvent stream 500 (e.g., carbon monoxide, epoxide) may be vented from the beta-lactone stream 400 and the catalyst solvent stream 500 in conjunction with one or more treatments 41, 51.

As described above, the beta-lactone may be recycled back to the carbonylation reactor 110, or the feed stream 100. In some embodiments, not all of the beta-lactone stream 420 is recycled. Some of the beta-lactone stream is withdrawn 430 and carried to acrylation step 3.

Acrylation

In some embodiments, the beta-lactone stream 430 resulting from the separation step 2 is optionally carried onto an acrylate production step. The acrylate production step is discussed in more detail below. The beta-lactone stream 430 may optionally be processed in a number ways prior to the acrylate production step. This processing can include, but is not limited to: heating, cooling, or compressing the stream; condensing the stream to a liquid state and carrying forward the liquid; adding a polymerization inhibitor to the stream; condensing selected components to a liquid state and carrying forward the remaining gaseous components; condensing selected components to a liquid state and carrying forward the liquefied components; scrubbing the stream to remove impurities; and any combination of two or more of these.

Turning next to the acrylate production step, the isolated beta-lactone stream 430 discussed above is carried onward to convert the beta lactone contained therein to acrylic acid or an acrylic acid derivative. As discussed above, in some embodiments, the isolated beta-lactone stream 430 may undergo additional processing steps between the separation step 2 and may enter the acrylate production stage of the process as a gas or as a liquid. The acrylate production step itself may be performed in either the gas phase or the liquid phase and may be performed either neat, or in the presence of a carrier gas, solvent or other diluent.

In certain embodiments, the acrylate production step is performed in a continuous flow format. In certain embodiments, the acrylate production step is performed in a continuous flow format in the gas phase. In certain embodiments, the acrylate production step is performed in a continuous flow format in the liquid phase. In certain embodiments, the acrylate production step is performed in a liquid phase in a batch or semi-batch format.

The acrylate production step may be performed under a variety of conditions. In certain embodiments, the reaction may be performed in the presence of one or more catalysts that facilitate one or more steps in the transformation of the beta lactone intermediate to the acrylate product. Many catalysts known in the art can be used, or adapted for this step. In some embodiments, conditions include reaction with dehydrating agents such as sulfuric acid, phosphoric acid or esters thereof as described in U.S. Pat. Nos. 2,352,641; 2,376,704; 2,449,995; 2,510,423; 2,623,067; 3,176,042, and in British Patent No. GB 994,091, the entirety of each of which is incorporated herein by reference.

In other embodiments, the lactone can be reacted with a halogenic compound to yield a beta halo acid, beta halo ester, or beta halo acid halide which may then undergo dehydrohalogenation and/or solvolysis to afford the corresponding acrylic acid or acrylic ester. In certain embodiments, conditions disclosed in U.S. Pat. No. 2,422,728 (incorporated herein by reference) are used in this process.

In other embodiments, the acrylate production may be base catalyzed, see for example *Journal of Organic Chemistry*, 57(1), 389-91(1992) and references therein, the entirety of which is incorporated herein by reference.

In certain embodiments, the acrylate production stage of the process may be performed by combining the isolated beta-lactone stream 430 from the previously described steps with an alcohol vapor and passing the mixture in the gas phase through a column of an solid, or solid supported promoter that affects the conversion to an acrylic ester. In certain embodiments, this process is performed over a promoter including activated carbon according to the methods of US Patent No. 2,466,501 the entirety of which is incorporated herein by reference.

In some embodiments, the beta lactone in the isolated beta-lactone stream 430 is allowed to polymerize and acrylic acid or derivatives thereof are obtained by decomposition of the polymer. In certain embodiments, the beta lactone is propiolactone and the polymer is poly(3-hydroxy propionic acid) (3-HPA). In certain embodiments, the 3-HPA is formed and decomposed using the methods described in U.S. Pat. Nos. 2,361,036; 2,499,988; 2,499,990; 2,526,554; 2,568,635; 2,568,636; 2,623,070; and 3,002,017, the entirety of each of which is incorporated herein by reference.

In certain embodiments, the beta lactone product stream is reacted with a nucleophile of the formula Y—H. In certain embodiments, Y is selected from the group consisting of halogen; —$OR^{13}$; —$NR^{11}R^{12}$; and —$SR^{13}$, where $R^{11}$, $R^{12}$, and $R^{13}$ are independently selected from the group consisting of: —H; optionally substituted $C_{1-32}$ aliphatic; optionally substituted $C_{1-32}$ heteroaliphatic; optionally substituted 3- to 14-membered carbocycle; and optionally substituted 3- to 14-membered heterocycle, and where $R^{11}$ and $R^{12}$ can optionally be taken together with intervening atoms to form an optionally substituted ring optionally containing one or more heteroatoms.

In certain embodiments, the beta lactone product stream is reacted with a nucleophile of the formula Y—H to afford an acrylate having the formula II:

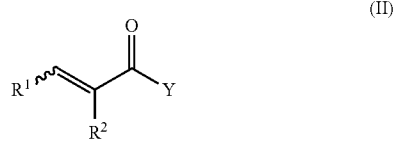

(II)

In certain embodiments, Y—H is an amine having the formula $R^{11}R^{12}N$—H, and the product is an acrylamide. In certain embodiments, conditions disclosed in U.S. Pat. Nos. 2,548,155; 2,649,438; 2,749,355; and 3,671,305, the entirety of each of which is incorporated herein by reference.

In certain embodiments, the beta lactone product stream is reacted with a nucleophile of the formula Y—H to afford an acid having the formula III:

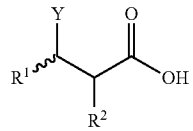

(III)

In certain embodiments, compounds of formula III are obtained using conditions disclosed in U.S. Pat. Nos. 2,449,992; 2,449,989; 2,449,991; 2,449,992; and 2,449,993, the entirety of each of which is incorporated herein by reference.

In certain embodiments, where the beta lactone product stream is reacted with a nucleophile of the formula Y—H to afford an acid having the formula III, and Y is —$OR^{13}$; —$NR^{11}R^{12}$; or —$SR^{13}$, the acid is dehydrated to yield an acrylate of formula II.

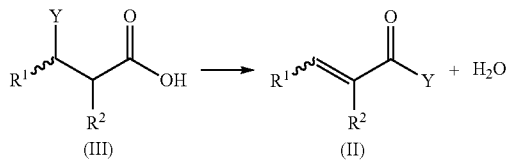

In certain embodiments, the conversion of III to II is performed according to the methods and conditions of U.S. Pat. No. 2,376,704 the entirety of which is incorporated herein by reference.

In certain embodiments, the acrylate product stream resulting from the proceeding steps may undergo additional purification steps. In certain embodiments, the stream is purified according to methods disclosed in U.S. Pat. Nos. 3,124,609; 3,157,693; 3,932,500; 4,82,652; 6,048,122; 6,048,128; 6,084,128; and 6,207,022, the entirety of each of which is incorporated herein by reference.

EXAMPLES

Several acronyms and abbreviations are used throughout this section. For clarity the most commonly are presented here. Ethylene Oxide ("EO"); Carbon Monoxide ("CO"); Propylene Oxide ("PO"); Turnover Frequency ("TOF"); Propiolactone or beta-Propiolactone ("PL:); Butyrolactone or beta-Butyrolactone ("BBL"); concentrations are indicated with brackets, e.g., concentration of Propiolactone [PL]; Freeze-Pump-Thaw ("FPT").

Example 1

Temperature and Pressure Effect

Temperature and pressure effect on carbonylation of EO was studied by varying temperature and pressure.

TABLE 1

Temperature and pressure effect on catalyst activity in THF

| rxn # | temp (° C.) | pressure (psi) | yield (%) | | | |
|---|---|---|---|---|---|---|
| | | | $EO^c$ | $Ald.^c$ | $PL^c$ | $SA^c$ |
| 29-39$^a$ | 30 | 200 | 69 | 0 | 22 | 0 |
| 29-56$^b$ | 60 | 200 | 0.4 | 5 | 92 | 0.1 |
| 29-59$^b$ | 30 | 600 | 44 | 0 | 44 | 0 |
| 29-54$^b$ | 60 | 600 | 0 | 0 | 88 | 8 |

TABLE 1-continued

Temperature and pressure effect on catalyst activity in THF

| rxn # | temp (° C.) | pressure (psi) | yield (%) | | | |
|---|---|---|---|---|---|---|
| | | | EO[c] | Ald.[c] | PL[c] | SA[c] |
| 29-57[b] | 60 | 600 | 0 | trace | 81 | 13 |
| 29-66[b] | 45 | 400 | 25 | trace | 73 | 0 |

* Conditions: EO (1.8M; Arc), catalyst: [(ClTPP)Al][Co(CO)4] (60 μmol), EO:cat = 1500:1, total volume: 50 mL (in THF), agitation speed: 730 rpm, reaction time: 3 h, and internal standard: hexamethylbenzene.
[a]catalyst: hexamethylbenzene (0.5 mmol; Alfa Aesar (Ward Hill, MA), and THF (received from the column; FPT *2)
[b]catalyst: hexamethylbenzene (1.0 mmol; TCI), and THF (dried over 4 Å sieves and stored in the glove box; FPT *2)
[c]EO (ethylene oxide), Ald. (acetaldehyde), PL (propiolactone), and SA (succinic anhydride)

Pressure increase from 200 psi of CO to 600 psi at 30° C. doubled the yield of propiolactone (see 29-39 and 29-59 in Table 1). When the reaction temperature was increased from 30° C. to 60° C. at 200 psi of CO (see 29-39 and 29-54), the reaction went to completion and the yield of propiolactone more than tripled.

Reaction Procedure A; Reaction Procedure for Carbonylation of Ethylene Oxide in THF A 300 mL Parr reactor was dried overnight under vacuum. In a nitrogen glovebox, the reactor was charged with [(ClTPP)Al][Co(CO)4] (66 mg, 60 mmol), hexamethylbenzene (162 mg, 1 0 mmol), and THF (dried over 4 Å molecular sieves, and freeze, pump, and thaw 3 times), then closed and removed from the glovebox. Ethylene oxide was vacuum transferred to a transfer vessel from EO lecture bottle. The Parr reactor was cooled to −78° C. and high vacuum was applied to the reactor. The vacuum was disconnected from the reactor, and the transfer vessel was connected to the Parr reactor to allow EO to be vacuum transferred from the transfer vessel to the reactor at −78° C. The reaction mixture was warmed to ambient temperature and saturated with CO by pressurizing the reactor with CO to three fourth of the desired CO pressure (e.g. 150 psi), then heated to the desired temperature. After the temperature of reaction mixture reached the desired temperature, the reactor was pressurized to the desired pressure (e.g. 200 psi). The reaction mixture was agitated for 3 h. The reactor was cooled to <0° C. and vented. A portion of reaction mixture was sampled and analyzed by 1H NMR in CDCl$_3$.

Example 2

Catalyst Loading

Catalyst concentration was doubled to see if the activity proportionally increases with the catalyst concentration increase (November 29-39 and 29-43 in Table 2).

TABLE 2

Reaction time and catalyst loading (30° C.; 200 psi CO)

| rxn # | time (h) | cat. (mmol) | EO/cat | yield (%) | | | | TOF (/h) |
|---|---|---|---|---|---|---|---|---|
| | | | | EO | Ald. | PL | SA | |
| 29-39 | 3 | 0.06 | 1500 | 69 | 0 | 22 | 0 | 110 |
| 29-38 | 6 | 0.06 | 1500 | 63 | 0 | 28 | 0 | 70 |
| 29-43 | 3 | 0.12 | 750 | 60 | 0 | 32 | 0 | 80 |

* Conditions: EO (1.8M), catalyst: [(ClTPP)Al][Co(CO)4] (60 μmol), EO:cat = 1500:1, total volume: 50 mL (in THF), agitation speed: 730 rpm, reaction time: 3 h, internal standard: hexamethylbenzene(0.5 mmol; Alfa Aesar), and THF (received from the column; FPT *2)

The same reaction procedure as Procedure A was used except for the catalyst loading.

Example 3

Evaluation of Syngas as a CO Source

Syngas is a cost-effective source for CO, and the use of syngas can reduce the cost of industrial scale ethylene oxide carbonylation. A one to one mixture of CO and H$_2$ was used to test ethylene oxide carbonylation (November 29-72 and November 29-73 in Table 3). No hydroformylation product, 3-hydroxypropanaldehyde or 1,3-propanediol, was found in $^1$H NMR spectrum of the reaction mixture.

TABLE 3

Syngas

| rxn # | CO:H$_2$ | temp (° C.) | pressure (psi) | yield (%) | | | |
|---|---|---|---|---|---|---|---|
| | | | | EO | Ald. | PL | SA |
| 29-39[a] | 100% CO | 30 | 200 | 69 | 0 | 22 | 0 |
| 29-72[b] | 1:1 | 30 | 200 | 47 | 0 | 8 | 0 |
| 29-73[b] | 1:1 | 30 | 400 | 53 | 0 | 10 | 0 |

* Conditions: EO (1.8M; Arc), catalyst: [(ClTPP)Al][Co(CO)4] (60 μmol), EO:cat = 1500:1, total volume: 50 mL (in THF), agitation speed: 730 rpm, reaction time: 3 h, and internal standard: hexamethylbenzene.
[a]catalyst: hexamethylbenzene (0.5 mmol; Alfa Aesar), and THF (received from the column; FPT *2)
[b]catalyst: hexamethylbenzene (1.0 mmol; TCI), and THF (dried over 4 Å sieves and stored in the glove box; FPT *2)

The same reaction procedure as Procedure A was used except for the CO source. The 50:50 mixture of CO and H$_2$ was purchased from Airgas (Radnor, PA) (Certified Grade; 50% Research Plus Grade CO and 50% Research Grade H$_2$).

Example 4

Carbonylation of Ethylene Oxide in High Boiling Point Solvents

The ethylene oxide carbonylation in high boiling point solvents was studied. In the continuous flow process of propiolactone production, propiolactone will be isolated by distillation from the reaction mixture, and this process needs a high boiling point solvent. Top three candidates for the high boiling point solvent were chosen based on the results from propylene oxide carbonylation. The catalyst activities of the reactions in three high boiling point solvents are about one fifth of the catalyst activity in THF (Table 4).

TABLE 4

High boiling solvents

| rxn # | solvent | temp (° C.) | pressure (psi) | yield (%) | | | |
|---|---|---|---|---|---|---|---|
| | | | | EO | Ald. | PL | SA |
| 29-56 | THF | 60 | 200 | 0.4 | 5 | 92 | 0.1 |
| 29-62 | DBE | 60 | 200 | 52 | 1.7 | 21 | 0 |
| 29-63 | Sulfolane | 60 | 200 | 41 | ? | 22 | ? |
| 29-64 | Pr. Carb. | 60 | 200 | 52 | trace | 15 | 0 |

* Conditions: EO (1.8M; Arc), catalyst: [(ClTPP)Al][Co(CO)4] (60 μmol), EO:cat = 1500:1; reaction time: 3 h; THF, DBE, sulfolane and propiocarbonate (dried over 4 Å sieves; ; FPT *2); and internal standard: hexamethylbenzene (1.0 mmol; TCI).

Reaction Procedure B; Reaction Procedure for Carbonylation of Ethylene Oxide in High Boiling Point Solvents A 300 mL Parr reactor was dried overnight under vacuum. In a nitrogen glovebox, the reactor was charged with [(ClTPP)Al][Co(CO)4] (66 mg, 60 mmol), and hexamethylbenzene (162 mg, 1.0 mmol), then closed and removed from the glovebox. Solvent (DBE, sulfolane or propylene carbonate; each solvent was dried over 4 Å molecular sieves and degassed) was added via syringe under $N_2$. Ethylene oxide was vacuum transferred to a transfer vessel from EO lecture bottle. The Parr reactor was cooled to −78° C. and high vacuum was applied to the reactor. The vacuum was disconnected from the reactor, and the transfer vessel was connected to the Parr reactor to allow EO to be vacuum transferred from the transfer vessel to the reactor at −78° C. The reaction mixture was warmed to ambient temperature and saturated with CO by pressurizing the reactor with CO to three fourth of the desired CO pressure (e.g. 150 psi), then heated to the desired temperature. After the temperature of reaction mixture reached the desired temperature, the reactor was pressurized to the desired pressure (e.g. 200 psi). The reaction mixture was agitated for 3 h. The reactor was cooled to <0° C. and vented. A portion of reaction mixture was sampled and analyzed by 1H NMR in $CDCl_3$.

Example 5

EO Carbonylation in DBE (Design of Experiments)

The goal of DOE was to find major factors influencing the activity of the catalyst ([(ClTPP)Al(THF)$_2$][Co(CO)$_4$]) and to find the optimum reaction conditions for running the EO carbonylation in DBE. DBE (a mixture of dimethyl succinate, dimethyl glutarate, and dimethyl adipate) was selected as the solvent of choice because the reaction in DBE showed the highest β-propiolactone (PL) yield among the preliminary high boiling point solvent screening reactions. Statistical software, JMP® 8.0, (SAS Software, Cary, N.C.) was used to design and analyze DOE runs. The experiment design was created using a screening design. Six continuous factors ([EO], temperature, CO pressure, agitation speed, time, and EO/catalyst ratio) were chosen for the DOE (Table 8). Fractional factorial type design having the six continuous factors was created. The design required 16 runs to analyze the effects of the six factors and some 2 factor interactions. Additional 3 center point runs were included to measure the variability of the DOE runs (Table 5).

TABLE 5

DOE factors; EO carbonylation in DBE

| Exp # | Pattern | [EO] (M) | EO/cat. | temp (° C.) | press (psi) | agitation (rpm) | time (h) |
|---|---|---|---|---|---|---|---|
| 1 | +----+ | 1.8 | 500 | 50 | 200 | 500 | 4 |
| 2 | +++--- | 1.8 | 1500 | 80 | 200 | 500 | 2 |
| 3 | 0 | 1.4 | 1000 | 65 | 400 | 750 | 3 |
| 4 | +--++- | 1.8 | 500 | 50 | 600 | 1000 | 2 |
| 5 | --+-++ | 1.0 | 500 | 80 | 200 | 1000 | 4 |
| 6 | 0 | 1.4 | 1000 | 65 | 400 | 750 | 3 |
| 7 | -++--+ | 1.0 | 1500 | 80 | 200 | 500 | 4 |
| 8 | ++-+-- | 1.8 | 1500 | 50 | 600 | 500 | 2 |
| 9 | ------ | 1.0 | 500 | 50 | 200 | 500 | 2 |
| 10 | -++++- | 1.0 | 1500 | 80 | 600 | 1000 | 2 |
| 11 | ++++++ | 1.8 | 1500 | 80 | 600 | 1000 | 4 |
| 12 | +-++-+ | 1.8 | 500 | 80 | 600 | 500 | 4 |
| 13 | --++-- | 1.0 | 500 | 80 | 600 | 500 | 2 |
| 14 | 0 | 1.4 | 1000 | 65 | 400 | 750 | 3 |
| 15 | -+---+ | 1.0 | 1500 | 50 | 200 | 1000 | 2 |
| 16 | +-+-+- | 1.8 | 500 | 80 | 200 | 1000 | 2 |
| 17 | -+-+-+ | 1.0 | 1500 | 50 | 600 | 500 | 4 |
| 18 | ---+++ | 1.0 | 500 | 50 | 600 | 1000 | 4 |
| 19 | ++--++ | 1.8 | 1500 | 50 | 200 | 1000 | 4 |

* Conditions: EO: purchased from Arc, catalyst: [(ClTPP)Al][Co(CO)$_4$], total volume: 60 mL, solvent: DBE (purchased from Aldrich; dried over 4 Å sieves; FPT *3; and stored in the glove box), internal standard: 1,4-di-tert-butylbenzene (1 mmol)

TABLE 6

DOE responses; EO carbonylation in DBE

| Exp # | Pattern | $Y_{Ald}$ (%) | $Y_{PL}$ (%) | $Y_{SA}$ (%) | $Y_{EO}$ (%) | $TOF_{PL}$ ($h^{-1}$) | $TOF_{CO}$ ($h^{-1}$) |
|---|---|---|---|---|---|---|---|
| 1 | +----+ | 0.6 | 36.6 | 0 | 28.1 | 46 | 46 |
| 2 | +++--- | 12.3 | 20.0 | 0 | 20.5 | 150 | 150 |
| 3 | 0 | 0.4 | 19.4 | 0 | 44.5 | 65 | 65 |
| 4 | +--++- | 0 | 34.5 | 0 | 40.7 | 86 | 86 |
| 5 | --+-++ | 30.3 | 0 | 54.2 | 0 | 0 | 136 |
| 6 | 0 | 0.6 | 23 | 0 | 38 | 77 | 77 |
| 7 | -++--+ | 35 | 35.5 | 0 | 0.8 | 133 | 133 |
| 8 | ++-+-- | 0 | 6.2 | 0 | 40.5 | 47 | 47 |
| 9 | ------ | 0.4 | 20 | 0 | 42.4 | 50 | 50 |
| 10 | -++++- | 2.4 | 20 | 0 | 39.2 | 150 | 150 |
| 11 | ++++++ | 3.3 | 33.2 | 0 | 27.8 | 125 | 125 |
| 12 | +-++-+ | 5.5 | 23.6 | 50.8 | 0.4? | 30 | 157 |
| 13 | --++-- | 5.4 | 0.7 | 68.8 | 0 | 2 | 346 |
| 14 | 0 | 0.4 | 23.6 | 0 | 26.5 | 79 | 79 |
| 15 | -+---+ | 0 | 5.3 | 0 | 41.8 | 40 | 40 |
| 16 | +-+-+- | 24.9 | 0 | 61.9 | 0 | 0 | 310 |
| 17 | -+-+-+ | 0 | 6.8 | 0 | 50.9 | 26 | 26 |
| 18 | ---+++ | 0 | 32.4 | 0 | 37 | 41 | 41 |
| 19 | ++--++ | 0 | 10.7 | 0 | 51.9 | 40 | 40 |

* $Y_{Ald}$: acetaldehyde yield based on $^1H$ NMR integration of acetaldehyde and internal standard (di-tert-butylbenzene); $Y_{PL}$: beta-propiolactone yield; $Y_{SA}$: succinic anhydride yield; $Y_{EO}$: percentage of EO left in the reaction mixture; $TOF_{PL} = Y_{PL}*[EO]_0/(time*[cat])$; and $TOF_{CO} = (Y_{PL}*[EO]_0 + Y_{SA}*[EO]_0)/(time*[cat])$.

Reaction Procedure C; Reaction Procedure for Carbonylation of Ethylene Oxide in DBE (DOE Runs; see Figures Below)

A 300 mL Parr reactor was dried overnight under vacuum. In a nitrogen glovebox, the reactor was charged with 1,4-di-tert-butylbenzene (190 mg, 1.0 mmol), and DBE (dried over 4 Å molecular sieves, and freeze, pump, and thaw 3 times). The shot tank which is connected to the reactor was charged with [(ClTPP)Al][Co(CO)$_4$] and 10 mL of DBE. The reactor was closed and removed from the glovebox. Ethylene oxide was vacuum transferred to a transfer vessel from EO lecture bottle. The Parr reactor was cooled to −78° C. and high vacuum was applied to the reactor. The vacuum was disconnected from the reactor, and the transfer vessel was connected to the Parr reactor to allow EO to be vacuum transferred from the transfer vessel to the reactor at −78° C. The reaction mixture was warmed to ambient temperature and the agitator was turned on. The reactor was heated to the desired temperature. After the temperature of reaction mixture reached the desired temperature, the shot tank was pressurized to three fourth of the desired CO pressure. The shot tank was open to the reactor to allow the catalyst solution to be added to the reactor. The reactor was pressurized to the desired pressure. The reaction mixture was agitated for indicated periods, and then it was cooled to −20° C. and vented. A portion of reaction mixture was sampled and analyzed by $^1H$ NMR in $CDCl_3$.

The responses for the DOE (Table 9) were acetaldehyde yield (%), PL yield (%), succinic anhydride (SA) yield (%), EO (%), $TOF_{PL}$ ((PL yield*[EO]$_0$)/(time*[cat])) and $TOF_{CO}$ (CO insertion per catalyst per hour).

Example 6

EO Carbonylation in Sulfolane at 80° C.

EO carbonylation in sulfolane was conducted at 80° C. to compare the reaction result with the carbonylations in DBE at 80° C. (Table 7). The reaction was run at the same reaction conditions as DOE run #13. Although, the CO insertion rate ($TOF_{CO}$) seems to be slower than that of DOE run #13, high PL yield and $TOF_{PL}$ suggests that sulfolane is the better solvent for ethylene oxide carbonylation.

TABLE 7

| [EO] (M) | EO/cat | temp (° C.) | press (psi) | agitate (rpm) | time (h) | $Y_{Ald}$ (%) | $Y_{PL}$ (%) | $Y_{SA}$ (%) | $Y_{EO}$ (%) | $TOF_{PL}$ ($h^{-1}$) |
|---|---|---|---|---|---|---|---|---|---|---|
| 1.0 | 500 | 80 | 600 | 500 | 2 | 2.4 | 80.4 | 0 | 1.1 | 201 |

* Conditions: EO: purchased from Arc, catalyst: [(ClTPP)Al][Co(CO)$_4$], total volume: 60 mL, solvent: sulfolane (purchased from Aldrich; dried over 4 Å sieves; FPT *3), internal standard: 1,4-di-tert-butylbenzene (1 mmol), the same reaction procedure as DOE runs.

The same reaction procedure as Procedure C was used except for the solvent. Sulfolane was purchased from Aldrich, dried over 4 Å sieves and FPT *3.

Example 7

Screening [(salph)M][Co(CO)$_4$] Catalysts

Catalysts having the structures shown in Formulas IV & V, were screened as catalyst candidate for EO carbonylation. While [(salph)Cr][Co(CO)$_4$] showed more than twice the activity of [(ClTPP)Al][Co(CO)$_4$], [(salph)Al][Co(CO)$_4$] showed much lower activity compared to [(salph)Cr][Co(CO)$_4$] (Table 11). The NMR analysis of the catalyst showed that the catalyst batch contains impurities.

Formulas IV & V.

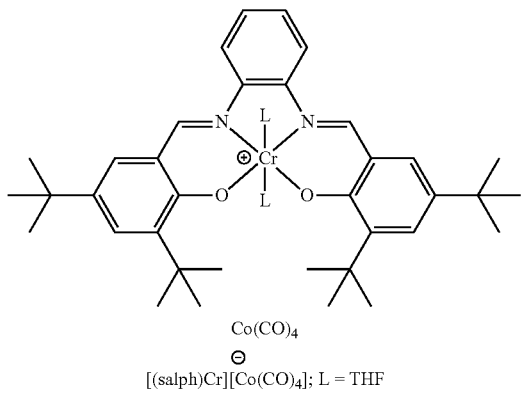

[(salph)Cr][Co(CO)$_4$]; L = THF

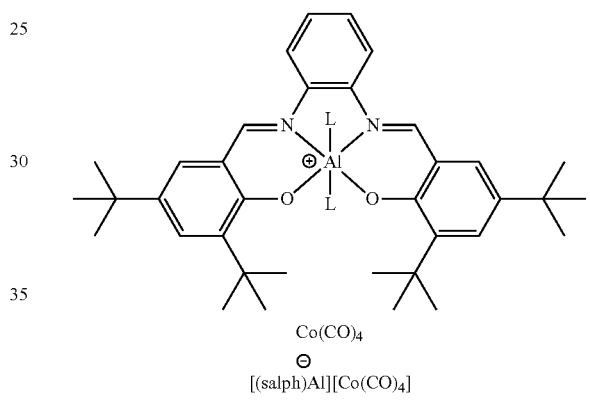

[(salph)Al][Co(CO)$_4$]

TABLE 8

| Exp. # | catalyst | EO/cat | temp (° C.) | press (psi) | $Y_{Ald}$ (%) | $Y_{PL}$ (%) | $Y_{SA}$ (%) | $Y_{EO}$ (%) | TOF ($h^{-1}$) |
|---|---|---|---|---|---|---|---|---|---|
| 29-85 | ClTPPAl[a] | 1000 | 65 | 400 | 0.6 | 23 | 0 | 38 | 77 |
| 29-102 | salphCr[b] | 1000 | 65 | 400 | 1.4 | 55.1 | 0 | 21 | 184 |
| 29-104 | salphAl[c] | 1000 | 65 | 400 | 0 | 3.5 | 0 | 44.1 | 12 |

[a]ClTPPAl = [(ClTPP)Al][Co(CO)$_4$]

[b]salphCr = [(salph)Cr][Co(CO)$_4$]

[c]salphAl = [(salph)Al][Co(CO)$_4$]

* Conditions: EO: purchased from Arc, [EO] = 1.4M, total volume: 60 mL, solvent: DBE (purchased from Aldrich; dried over 4 Å sieves; FPT *3), internal standard: 1,4-di-tert-butylbenzene (1 mmol), the same reaction procedure as DOE runs.

The same reaction procedure as Procedure C was used except for the catalyst.

Example 8

React-IR Experiments in DBE and Sulfolane

Figure 3:
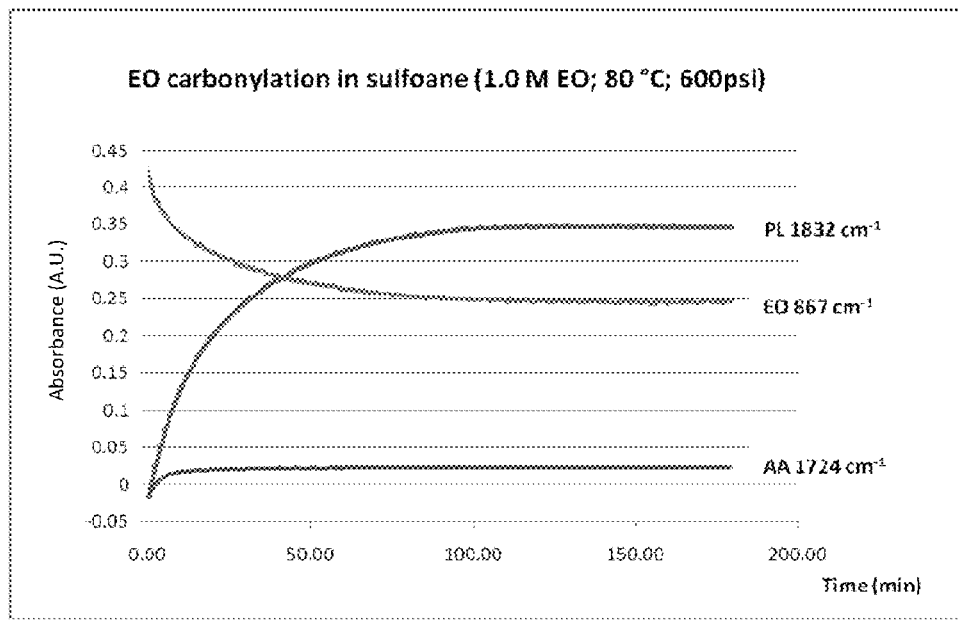
FIG. 3 is a graph of absorbance of propriolactone (1823 cm-1), ethylene oxide (867 cm-1), and acetaldehyde (1724 cm-1) monitored during the carbonylation reaction in sulfolane, with a starting concentration of ethylene oxide of 1.0 M.
Figure 4:
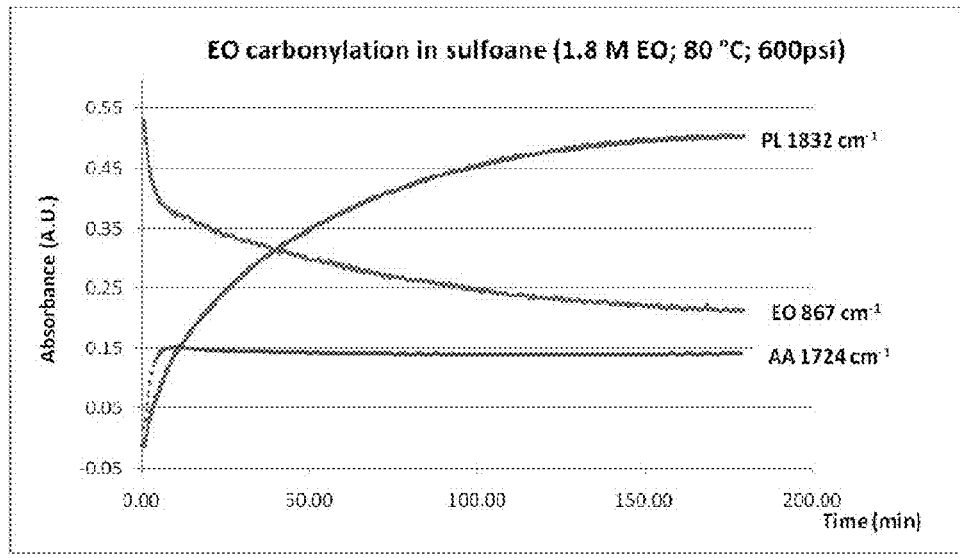
FIG. 4 is a graph of absorbance of propriolactone (1823 cm-1), ethylene oxide (867 cm-1), and acetaldehyde (1724 cm-1) monitored during the carbonylation reaction in sulfolane with a starting concentration of ethylene oxide of 1.8 M.

A react-IR probe was used to monitor EO carbonylations in DBE and sulfolane. Two reactions in sulfolane were monitored by react-IR (November 29-105 and November 29-108; Table 9). Absorbance of PL (1823 cm$^{-1}$), EO (867 cm$^{-1}$), and acetaldehyde (1724 cm$^{-1}$) was monitored during the reactions and absorbance versus time plot is shown in FIGS. 3 and 4.

The EO carbonylation in DBE was also monitored using react-IR (Table 10). The reaction procedure for this reaction was modified from the DOE experiment procedure to avoid acetaldehyde formation. The catalyst solution in DBE was pressurized to 200 psi for 40 min in a Parr reactor. The temperature was increased from room temperature to 80° C., while the reactor was pressurized to 200 psi. EO was added to a shot tank, and then the shot tank was pressurized with CO to 600 psi. EO was added to the Parr reactor by opening the valve connecting the shot tank and the Parr reactor. Despite the pre-saturation of the reaction mixture with CO, $^1$H NMR analysis of the sample taken after the reaction shows that acetaldehyde was produced in the reaction.

TABLE 9

| Exp. # | [EO] (M) | EO/cat | temp (° C.) | press (psi) | agitate (rpm) | $Y_{Ald}$ (%) | $Y_{PL}$ (%) | $Y_{SA}$ (%) | $Y_{EO}$ (%) |
| --- | --- | --- | --- | --- | --- | --- | --- | --- | --- |
| 29-105 | 1.0 | 500 | 80 | 600 | 500 | 3.8 | 53.6 | 0 | 1.4 |
| 29-108 | 1.8 | 500 | 80 | 600 | 500 | 7.9 | 46.8 | 0 | 3.2 |

* Conditions: EO: purchased from Arc, catalyst: [(ClTPP)Al][Co(CO)$_4$] total volume: 108 mL, solvent: sulfolane (purchased from Aldrich; dried over 4 Å sieves; FPT *3), internal standard: 1,4-di-tert-butylbenzene (1 mmol)

Reaction Procedure D; Reaction Procedure for Carbonylation of Ethylene Oxide in DBE Monitored by React-IR In a nitrogen glovebox, a 300 mL Parr reactor equipped with IR sentinel probe was charged with 1,4-di-tert-butyl-

TABLE 10

| Exp. # | [EO] (M) | EO/cat | temp (° C.) | press (psi) | agitate (rpm) | $Y_{Ald}$ (%) | $Y_{PL}$ (%) | $Y_{SA}$ (%) | $Y_{EO}$ (%) |
| --- | --- | --- | --- | --- | --- | --- | --- | --- | --- |
| 29-112 | 1.0 | 500 | 80 | 600 | 500 | 7.9 | 0 | 62.7 | 0 |

* Conditions: solvent: DBE (purchased from Aldrich; dried over 4 Å sieves; FPT *3), EO: purchased from Arc, catalyst: [(ClTPP)Al][Co(CO)$_4$], total volume: 100 mL, internal standard: 1,4-bis(trimethylsilyl)benzene (1.11 mmol).

benzene (190 mg, 1.0 mmol). The reactor was closed and removed from the glovebox. The IR sentinel probe was connected to a react IR (Mettler-Toledo, Columbus, Ohio). Sulfolane (dried over 4 Å molecular sieves, and degassed) was added to the reactor via syringe under N$_2$. Ethylene oxide was vacuum transferred to a transfer vessel from EO lecture bottle. The Parr reactor was cooled 0° C. and high vacuum was applied to the reactor. The vacuum was disconnected from the reactor, and the transfer vessel was connected to the Parr reactor to allow EO to be vacuum transferred from the transfer vessel to the reactor. The reaction mixture was warmed to ambient temperature and the agitator was turned on. A shot tank was connected to the reactor and was charged with [(ClTPP)Al][Co(CO)$_4$] and 10 mL of sulfolane. The reactor was heated to the desired temperature. After the temperature of reaction mixture reached the desired temperature, the shot tank was pressurized to three fourth of the desired CO pressure. The shot tank was open to the reactor to allow the catalyst solution to be added to the reactor. The reactor was pressurized to the desired pressure. The reaction was monitored by react-IR.

No succinic anhydride (FIG. 3; Table 9) was formed even long after PL formation plateaued.

The same reaction procedure as Procedure D was used except for the solvent.

Figure 5:
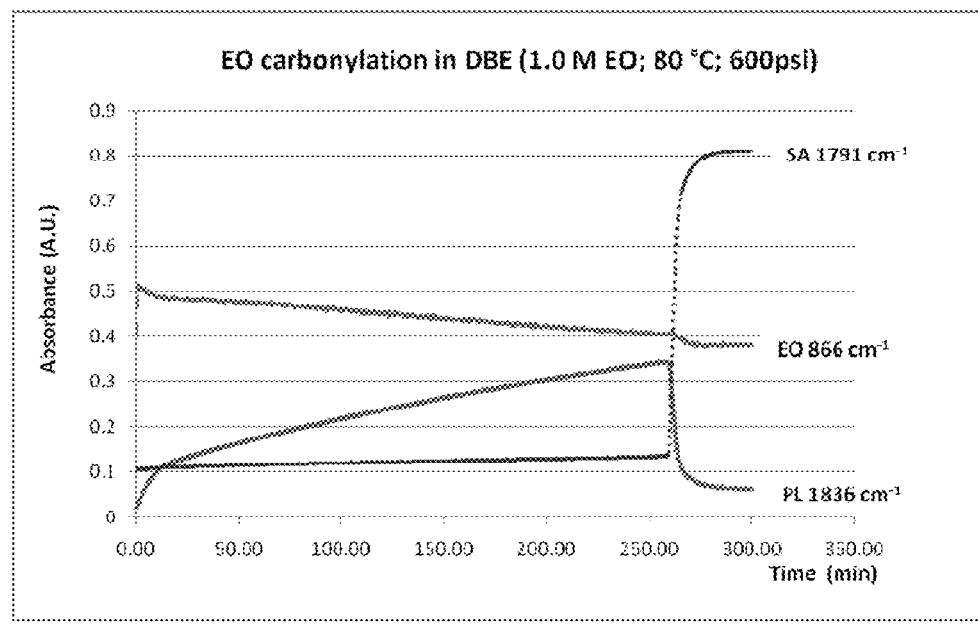
FIG. 5 is a graph of absorbance of propriolactone (1823 cm-1), ethylene oxide (867 cm-1), and acetaldehyde (1724 cm-1) monitored during the carbonylation reaction in dibasic ester.

Absorbance of PL (1823 cm$^{-1}$), EO (867 cm$^{-1}$), and SA (1791 cm$^{-1}$) is plotted as a function time and shown in FIG. 5. Acetaldehyde (1724 cm$^{-1}$) peak was overlapped with DBE peaks and could not be monitored. The plot shows that the 2nd carbonylation (conversion from PL to SA) undergoes much faster than 1st carbonylation (from EO to PL) in DBE.

Example 9

Effect of Initial Addition of β-Propiolactone (PL)

Externally adding PL into the reaction mixture before the start of the reaction was tested using react-IR. Using PL as a solvent or a co-solvent is an attractive idea for the commercial scale process of EO carbonylation because it can facilitate the separation of PL. However, PL itself can react with CO to produce SA. The 1.0 M PL solution in sulfolane containing the catalyst was pre-saturated with 200 psi of CO for 40 min, and then EO was added to the catalyst solution with 400 psi of CO.

TABLE 11

| Exp. # | [EO] (M) | EO/cat | temp (° C.) | press (psi) | agitate (rpm) | $Y_{Ald}$ (%) | $Y_{PL}$ (%) | $Y_{SA}$ (%) | $Y_{EO}$ (%) |
|---|---|---|---|---|---|---|---|---|---|
| 29-110 | 1.8 | 500 | 80 | 400 | 500 | 9.1 | 34.5 | 0 | 5.0 |

*Conditions: EO: purchased from Arc, catalyst: [(ClTPP)Al][Co(CO)$_4$], total volume: 100 mL, solvent: sulfolane (purchased from Aldrich; dried over 4 Å sieves; degassed), PL (purchased from Aldrich; dried over 4 Å sieves; degassed), internal standard: 1,4-bis(trimethylsilyl)benzene (1.11 mmol).

Reaction Procedure E; Reaction Procedure for Carbonylation of Ethylene Oxide in PL and Sulfolane Monitored by React-IR In a nitrogen glovebox, a 300 mL Parr reactor equipped with IR sentinel probe was charged with 1,4-bis(trimethylsilyl)benzene (1.11 mmol) and [(ClTPP)Al][Co(CO)$_4$] (0.36 mmol). The reactor was closed and removed from the glovebox. The IR sentinel probe was connected to a react IR. Sulfolane (dried over 4 Å molecular sieves, and degassed) and PL (purchased from Aldrich; dried over 4 Å sieves; FPT*3), were added to the reactor via syringe under N$_2$. The agitator was turned on, and the reaction mixture was heated to the desired temperature. A shot tank was connected to the reactor and was charged with ethylene oxide. After the temperature of reaction mixture reached the desired temperature, the shot tank was pressurized to three fourth of the desired CO pressure. The shot tank was open to the reactor to allow EO to be added to the reactor. The reactor was pressurized to the desired pressure. The reaction was monitored by react-IR.

No formation of SA was observed in $^1$H NMR, which means that PL did not react with CO in the presence of the catalyst during the pre-saturation step and during the reaction (temperature was ramped up from room temperature to 80° C. for 40 min during the pre-saturation step).

Figure 6:
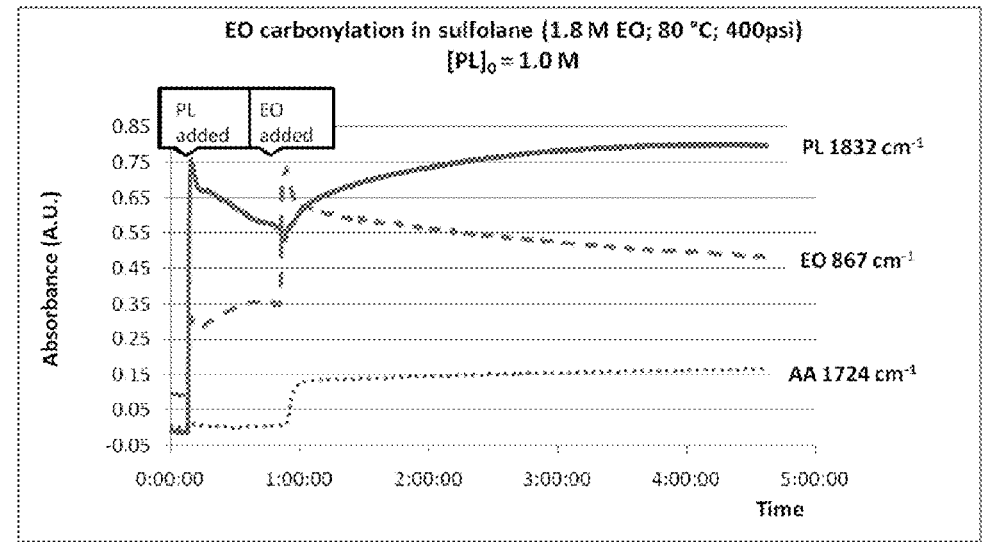
FIG. 6 is a graph of absorbance of propriolactone (1823 cm-1), ethylene oxide (867 cm-1), and SA (1791 cm-1) monitored during the carbonylation reaction in sulfolane with additional propriolactone and ethylene oxide added during the reaction.

The absorbance of PL, EO, and acetaldehyde was monitored during the reaction (FIG. 6). Even after the pre-saturation with CO, the absorbance of acetaldehyde rose quickly when EO was added, and then slowly increased after the first steep increase.

Example 10

β-Propiolactone Concentration Effect on Catalyst Activity

To understand how catalyst behaves in high PL content, we studied effect of [PL] on catalyst activity.

A. β-Propiolactone Concentration Effect on Catalyst Activity in Sulfolane

PL, which was purchased from Aldrich, dried over 4 Å molecular sieves, and FPT 3 times, was used as a co-solvent to study effect of PL concentration on catalyst activity in sulfolane (Table 12). The catalyst activity was measured by react-IR.

TABLE 12

| Exp. # | [PL]$_0$ (M) | PL weight % | initial rate* (M/h) |
|---|---|---|---|
| 29-128 | 0 | 0 | 1.97 |
| 29-120 | 1.1 | 6.6 | 0.93 |
| 29-119 | 2.2 | 13.3 | 0.50 |

*Conditions: EO: purchased from Arc 1.8M, catalyst: [(ClTPP)Al][Co(CO)$_4$] 0.36 mmol, solvent: sulfolane (purchased from Aldrich; dried over 4 Å sieves; degassed), agitation 500 rpm, total volume 100 mL; temp 65° C.; CO pressure 400 psi
*Procedure: EO was added with 400 psi of CO to a reaction mixture containing catalyst, sulfolane, and PL at 65° C.
*Initial rate: rate of PL formation during the first 5 min The same reaction procedure as Procedure E was used except for the amount of PL.

Figure 7:
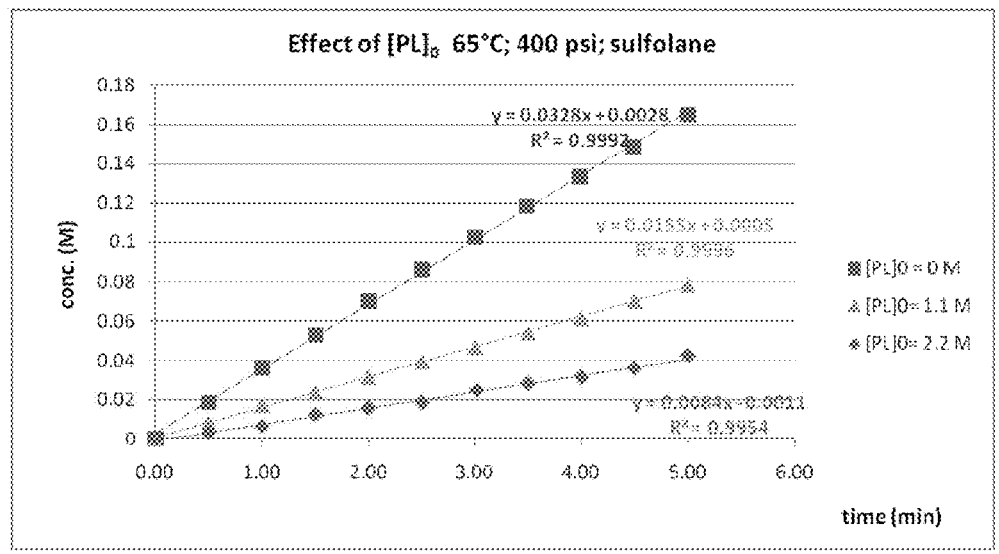
FIG. 7 is a graph of showing the formation of propriolactone during the first 5 min of the ethylene oxide carbonylation for various concentrations of propriolactone recycle.

The formation of PL during the first 5 min of the EO carbonylation was plotted as a function of time (FIG. 7), and the PL formation rate was calculated from the slope of the line. Absorbance of PL was converted to concentration by using the following equation from linear square fitting of [PL] and IR absorbance.

[PL]=2.4367 AU−0.081(AU=Absorbance unit)

As shown in Table 15, the catalyst activity is reduced at higher [PL] and is highly dependent on [PL].

Example 11

β-Propiolactone Concentration Effect on Catalyst Activity in THF

Instead of adding PL before the reaction, PL was converted from EO and accumulated to a certain level. The second batch of catalyst was added in the middle of EO carbonylation when [PL] reached at a certain level. The PL formation rate at that point was measured by react-IR. Also, THF was used as solvent to increase activity and meet the targeted PL formation rate.

Figure 8:
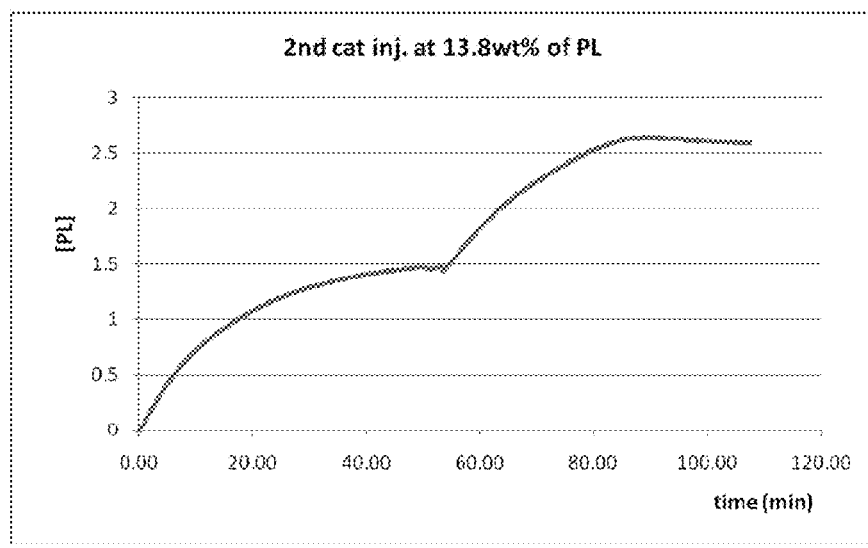
FIG. 8 is a graph of propriolactone concentration for a reaction run with a second catalyst injection at 13.8% percent propriolactone.

One of the reaction profiles from the reactions that were run to calculate catalyst activity (29-135) is shown in FIG. 8. The reaction was started by adding EO with 600 psi of CO to a mixture of catalyst and THF at 65° C. (point A in FIG. 8). The reaction was monitored by react-IR and when PL content reached 13.8 wt %, 2$^{nd}$ batch of catalyst (0.18 mmol) was added to the reaction mixture with 600 psi of CO (point B in FIG. 8).

By subtracting the PL formation rate right before point B from the PL formation rate right after point B, the catalyst activity at 13.8 wt % of PL (1.76 M) was obtained. Using the similar experimental procedure and calculation method, the catalyst activity at 24.5 wt % was also obtained (Table 16).

TABLE 13

PL formation rate (catalyst 1.8 mM; 65° C.; 600 psi of CO)

| Exp # | [PL] (M) | PL wt % | PL form rate (M/h) |
|---|---|---|---|
| 29-135 | 0 | 0 | 5.21 |
| 29-135 | 1.76 | 13.8 | 3.26 |
| 29-137 | 3.20 | 24.5 | 2.17 |

The absorbance unit from PL peak at 1832 cm$^{-1}$ was converted to concentration using the equation shown below. A plot of [PL] versus IR absorbance unit showed that as [PL] gets close to 3 M, the relationship between IR absorbance and [PL] deviated from the linearity. Therefore, a polynomial best fit was used to obtain the conversion equation.

[PL]=0.5075*AU$^3$−0.0573*AU$^2$+2.0525*AU+0.0028
(AU=Absorbance unit)

Example 12

Carbonylation of Propylene Oxide

The carbonylation of propylene oxide was studied by varying temperature, CO pressure, and solvent. Propylene oxide was reacted with carbon monoxide in a 300 mL Parr reactor containing [(ClTPP)Al][Co(CO)$_4$], hexamethyl benzene (internal standard), and solvent.

TABLE 14

| solvent | temp °C. | pressure psi | PO % | β-butyrolactone | acetone % |
|---|---|---|---|---|---|
| dioxane | 90 | 200 | 21 | 37 | 15[b] |
| dioxane | 30 | 200 | 60 | 34 | 0 |
| dioxane | 30 | 800 | 46 | 39 | 0 |
| THF | 30 | 200 | 49 | 43 | 0 |
| THF | 55 | 200 | 0 | 97 | 0 |
| THF | 30 | 800 | 8 | 91 | 0 |

* conditions: [propylene oxide] = 90 mmol (1.8M), [(ClTPP)Al][Co(CO)$_4$] = 0.06 mmol (1.2 mM), 3 h
* no succinic anhydride was observed in these reactions.
[a] yields are based on $^1$H NMR integration of PO, β-butyrolactone, acetone and internal standard (hexamethylbenzene)
[b] the reaction mixture was not pre-saturated with CO before adding PO As shown in the table above, the higher yields of β-butyrolactone were attained in THF compared to those in 1,4-dioxane, and the highest yield was obtained from the reaction in THF at 55° C. under 200 psi of CO.

Figure 9:
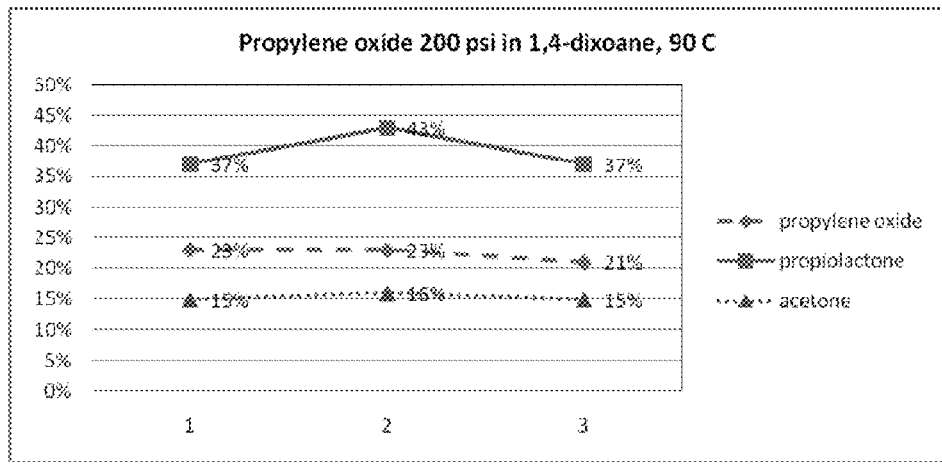
FIG. 9 is a graph of concentration of propylene oxide, propiolactone and acetone for a series of carbonylation reactions at 200 psi in 1,4 Dioxane at 90° C.
Figure 10:
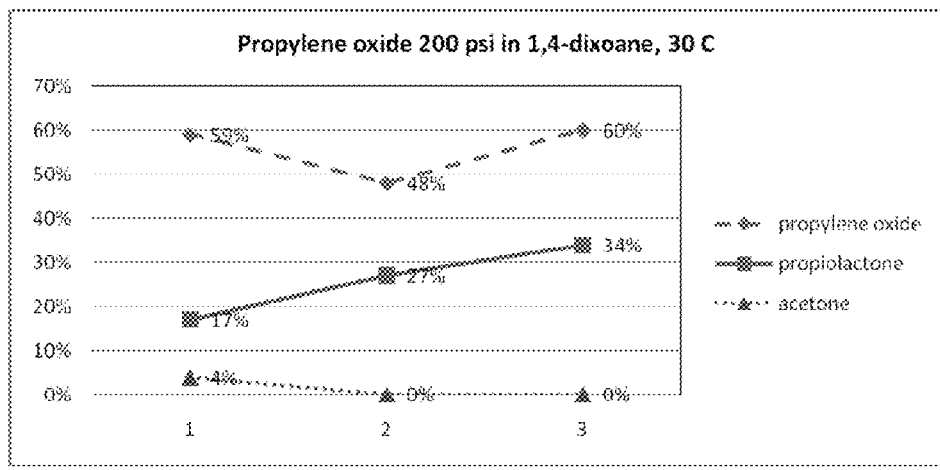
FIG. 10 is a graph of concentration of propylene oxide, propiolactone and acetone for a series of carbonylation reactions at 200 psi in 1,4 Dioxane at 30° C.

Two reactions in 1,4-dioxane under 200 psi CO pressure at 90° C. and 30° C. were monitored every hour for three hours by sampling the reaction mixture. As shown in FIGS. 9 and 10, the percentage of propiolactone in the reaction mixture at 90° C. does not increase after 1h while that in the reaction mixture at 30° C. steadily increases over time, which suggests that the catalyst is deactivated at 90° C. during the first hour of the reaction.

Representative Reaction Procedure for Carbonylation of Propylene Oxide

A 300 mL Parr reactor was dried overnight under vacuum. In a nitrogen glovebox, the reactor was charged with [(ClTPP)Al] [Co(CO)$_4$] (66 mg, 60 μmol) and hexamethylbenzene (81 mg, 0.50 mmol), then closed and removed from the glovebox. Solvent was added via syringe under N$_2$. The reaction mixture was saturated with CO by pressurizing the reactor with CO to ~15 psi. Propylene oxide (6.3 mL, 90 mmol) was added to the reactor via syringe. The reactor was pressurized with CO to three fourth of the desired CO pressure (e.g. 150 psi), then heated to the desired temperature. After the temperature of reaction mixture reached the desired temperature, the reactor was pressurized to the desired pressure (e.g. 200 psi). The reaction mixture was agitated for 3 h. The reactor was cooled to <0° C. and vented. A portion of reaction mixture was sampled and analyzed by $^1$H NMR in CDCl$_3$.

Example 13

High Boiling Solvent—Solvent Screening

Solvents were selected for the screening process based predominately upon boiling point. For efficient separation from propiolactone (b.p.=160° C.), a 30 degree boiling point difference was sought. The initial screening included dibasic ester (DBE), N-methylpyrrolidinone (NMP), triglyme, propylene carbonate, and sulfolane. Propylene oxide was used as a model for ethylene oxide, due to ease of use.

Solvent parameters such as dielectric constant, dipole moment, donor number, and CO solubility were collected and compared to the demonstrated activity (tested in the Endeavor reactor, Table 15).

TABLE 15

High-Boiling Solvent Screening

| Solvent | Boiling point (° C.) | Dielectric constant | Dipole moment | Donor number [a] (kcal/mol) | CO solubility (mM) | Activity[b] (TO/h) |
|---|---|---|---|---|---|---|
| THF | 65-57 | 7.58 | 1.6 | 20 | 21.61 | 340[b] 243[c] |
| Acetonitrile | 81-82 | 37.5 | 3.92 | 14.1 | 7.42 | 0[b] |
| DME | 85 | Low | 1.31 | 20 | 33.14 | 88[b] |
| 1,4-Dioxane | 100-102 | 2.2 | 0.4 | 14.8 | 34.20 | 100[b] |
| Toluene | 110 | 2.4 | 1.3 | ~0 | 37.78 | 3.4[b] |
| DBE | 196-225 | 7.7 | 0.5-1.2 | 17.1[d] | 20.28 | 55[c] |
| DBE-3 | 215-225 | | | 17.1[d] | 25.05 | 68[c] |
| NMP | 202 | 33 | 4.1 | 27.3 | 19.22 | 0[c] |
| Triglyme | 216 | 7.53 | 2.2 | 14 | 22.53 | 6.3[c] |
| Tetraglyme | 275 | | | | 20.41 | 8[c] |
| Propylene Carbonate | 240 | 64.4 | 4.94 | 15.1 | 11.13 | 24[c] |
| Sulfolane | 285 | 43.3 | 4.8 | 14.8 | 8.75 | 45[c] |
| Phenyl Ether | 259 | 3.9 | 1.47 | | 17.76 | 18[c] |
| Benzyl Ether | 298 | | 1.65 | | 14.45 | 6[c] |
| Phthalan | 192 | | | | | 73[c] |
| Propylene Oxide | 34 | | | | 48.38 | ND |
| β-Butyrolactone | ~160 | | | | 25.05 | ND |
| Tetrahydrofurfurylaceate | 194-195 (753 mmHg) | | | | | ND |

[a] Donor number is a measure of the ability to solvate cations. It is the negative enthalpy value for a 1:1 adduct formation between the Lewis base and SbCl$_5$ in dilute solution in C$_2$H$_4$Cl$_2$.
[b] Reaction conditions: Parr reactor, [PO] = 1.0M, [Cat]:[PO] = 500, 40° C., 850 psi CO.
[c] Reaction conditions: Endeavor, [PO] = 1.8M, [Cat]:[PO] = 500, 40° C., 200 psi CO.
[d] Reported value is for ethyl acetate.

Solvent Selection and Optimization

Out of all of the solvents screened for the carbonylation of propylene oxide, dibasic ester and sulfolane were chosen to pursue further studies. Simple adjustments to reaction temperature and pressure were made, resulting in improved activity in both cases (Table 21). The catalyst shows lower activity in sulfolane in general, however increases in temperature and CO pressure significantly improve the activity. Additionally, carbonylation in a mixture of THF and sulfolane (entry 5) also shows improved activity. In all cases, carbonylation in sulfolane is highly selective, with no observable byproducts such as methylsuccinic anhydride.

TABLE 16

Carbonylation of PO in high boiling solvents.[a]

| Expt | Solvent | [PO]:[Cat] | Temperature (° C.) | Pressure (psi) | Activity (TO/h) |
|---|---|---|---|---|---|
| 1 | Sulfolane | 500 | 40 | 200 | 45 |
| 2 | Sulfolane | 500 | 60 | 200 | 132 |
| 3 | Sulfolane | 500 | 60 | 400 | 195 |
| 4 | Sulfolane | 500 | 90 | 400 | 358 |
| 5 | Sulfolane/THF | 500 | 40 | 200 | 61 |
| 6 | DBE | 500 | 40 | 200 | 84 |
| 7 | DBE | 500 | 60 | 200 | 198 |
| 8 | DBE | 500 | 60 | 400 | 279 |
| 9 | DBE | 250 | 60 | 400 | 290 |

[a]Reaction conditions: Endeavor reactor, [PO] = 1.8M, 5 mL solution volume.

Figure 11:
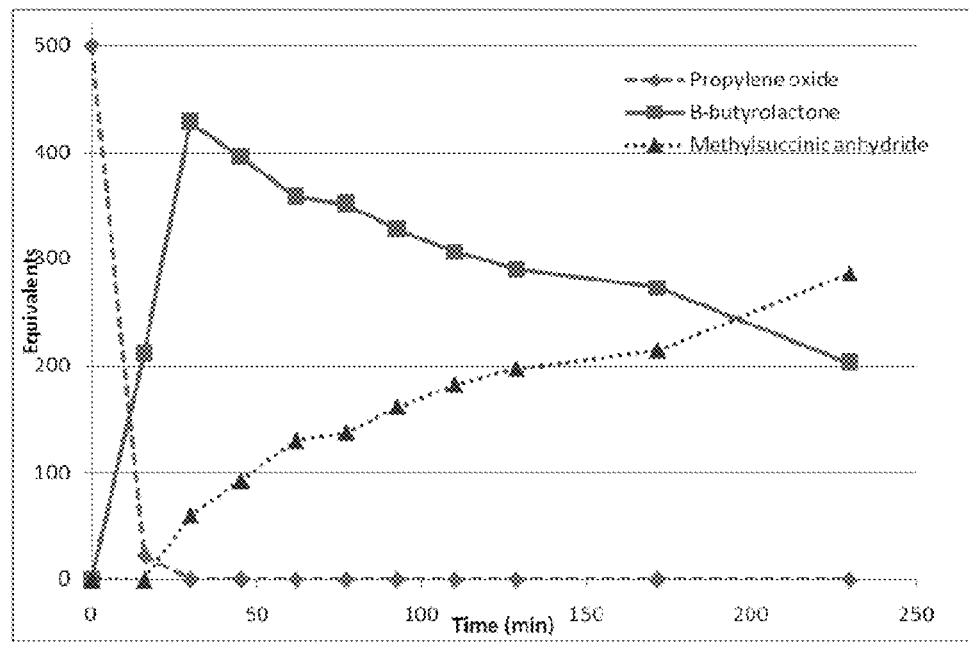
FIG. 11 is a graph of the concentrations of propylene oxide ("PO"), b-butyrolactone and methylsuccinic anhydride during the carbonylation of PO in DBE-3. Reaction conditions: Parr reactor, [PO]=1.8 M, [PO]:[cat]=500, 60° C. (up to 77° C.), 400 psi CO.
Figure 12:
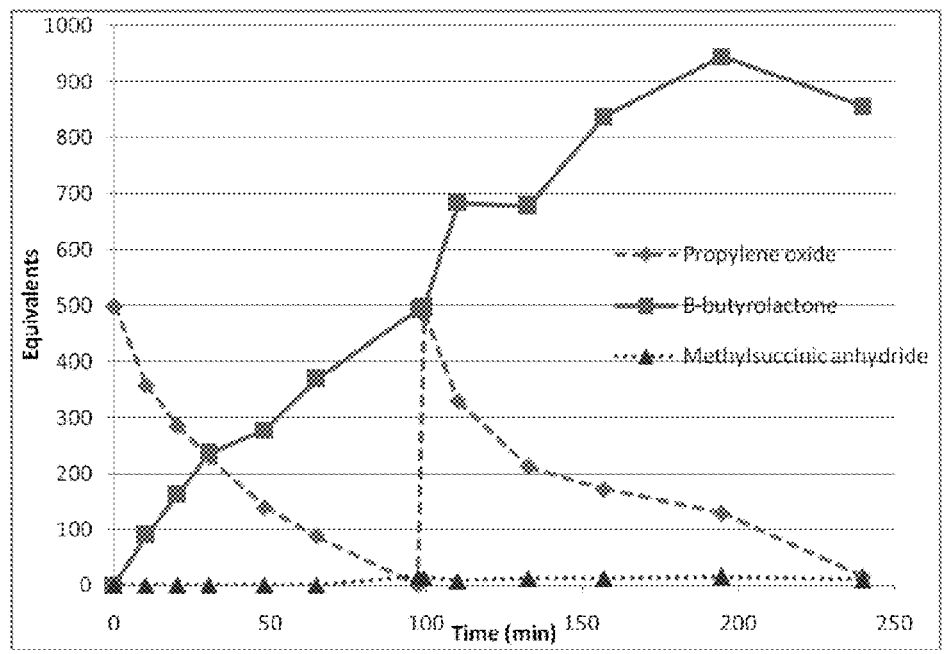
FIG. 12 is a graph of the concentrations of propylene oxide ("PO"), beta-butyrolactone and methylsuccinic anhydride during the carbonylation of PO in DBE-3. Reaction conditions: Parr reactor, [PO]=1.8 M, [PO]:[cat]=500, 60° C., 400 psi CO. A second PO injection was performed at 100 min.

Carbonylation rates in DBE are also improved by increasing the temperature and CO pressure. However, selectivity in DBE is not as high as in sulfolane. Significant amounts of methylsuccinic anhydride are formed, particularly at higher temperatures (FIG. 11). It should be noted that the temperature control in the beginning of this reaction was difficult, reaching as high as 77° C. in the first 45 min. It appears that lactone and anhydride formation is sequential and not simultaneous. Repetition of this experiment (FIG. 12) with better temperature control results in slower overall reaction, including slower anhydride formation. A small amount of anhydride was formed when an additional injection of propylene oxide is performed. At this point lactone formation appears to proceed at the same rate, while the anhydride concentration remains constant, lending further support to the theory that anhydride is only formed after the vast majority of epoxide is consumed. This behavior indicates that with the right conditions it will be possible to synthesize the lactone in high yields in DBE with minimal accumulation of the anhydride.

Scheme 6 Carbonylation of propylene oxide

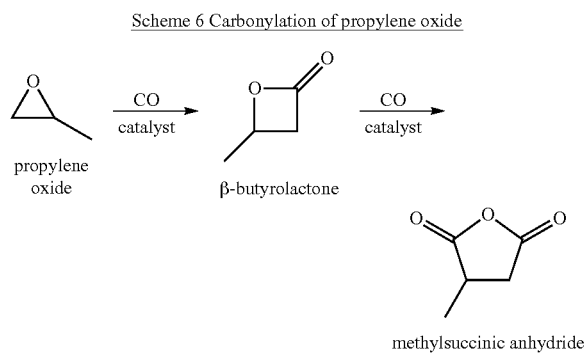

propylene oxide    β-butyrolactone methylsuccinic anhydride

Example 14

Catalyst Longevity

Preliminary Screening

Figure 13:
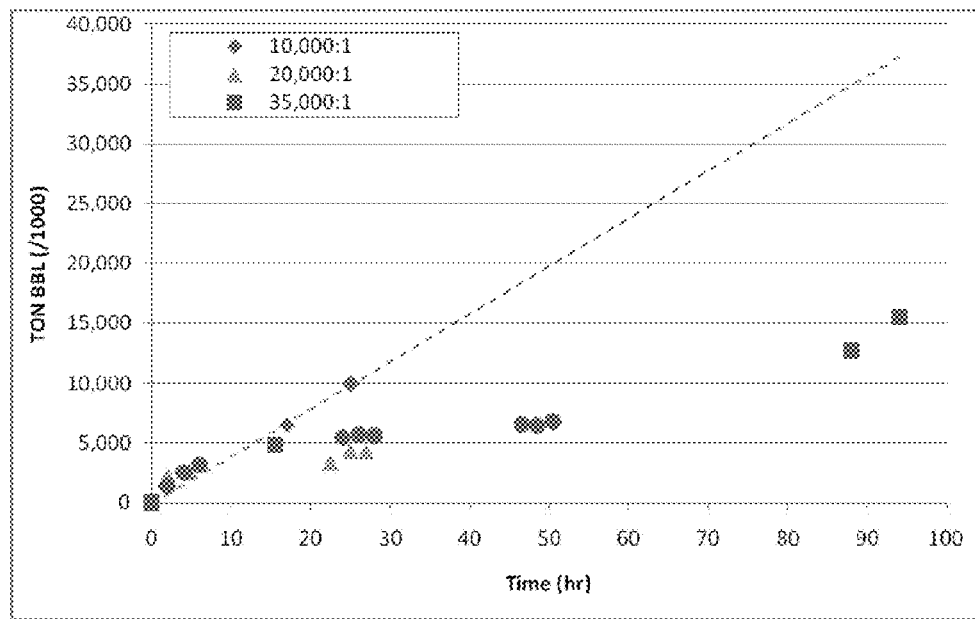
FIG. 13 is graph of the concentration of beta-butyrolactone in a series of carbonylation reactions of PO in THF. Reaction conditions: Parr reactor, [PO]=1.8 M, 55° C. with varying catalyst to oxide ratios.

In order to analyze the length of time the catalyst could maintain activity, a simple experiment with very low catalyst loadings ([PO]:[cat]=10,000) was performed (Table 23, entry 1). The reaction reached completion within 25 h, and samples late in the reaction suggest a linear rate of conversion with time (FIG. 13). Carbonylation of PO under higher catalyst loadings typically give turnover frequencies (TOFs) around 500 TO/h, and even with the low catalyst loadings a TOF of 400 TO/h was obtained.

TABLE 17

Carbonylation of PO in THF at low catalyst loadings[a]

| Entry | [PO]:[cat] | CO pressure (psi) | Time (h) | TON (mol BBL/mol cat) | % yield |
|---|---|---|---|---|---|
| 1 | 10,000 | 200 | 25 | 10,000 | 100 |
| 2 | 20,000 | 400 | 27 | 4370 | 21.9 |
| 3 | 35,000 | 200 | 94 | 15,500 | 44.3 |
| 4 | 35,000 | 200 | 50.5 | 6,780 | 19.4 |

[a]Reaction conditions: Parr reactor, [PO] = 1.8M, 55° C., THF.

A significant deviation from linear conversion is noted at [PO]:[cat]=20,000-35,000. Possible causes for this deviation include, impurities in the solvent or substrate which may be more influential with respect to the reaction outcome at low catalyst loadings. It is also possible that the product lactone could inhibit the carbonylation reaction by competing with the epoxide for access to the catalyst. And finally, CO solubility is much lower in the lactone than in the epoxide, so as the reaction progresses, the concentration of CO could diminish.

Sequential Monomer Addition

Figure 14:
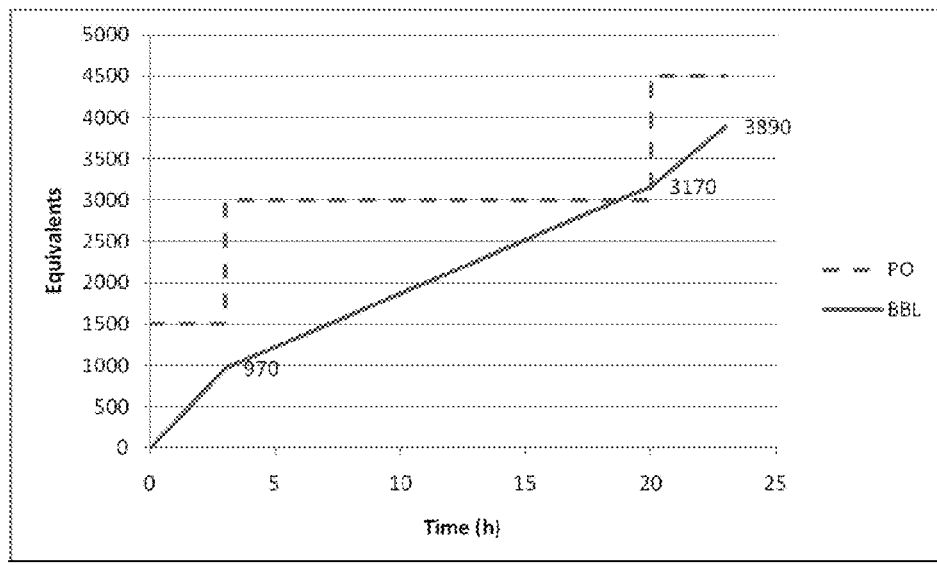
FIG. 14 is a graph of the concentrations of propylene oxide ("PO") and beta-butyrolactone ("BBL") during a carbonylation of PO in THF. Reaction conditions: Parr reactor, [PO]=1.8 M, [PO]:[cat]=1500, 55° C., 200 psi CO. Additional PO injections were performed at 3 h and 20 h.

To evaluate cyclical and/or continuous processes an experiment with a series of monomer additions was performed. The reaction was allowed to proceed to completion (3 hours), at which point another aliquot of substrate was added (FIG. 14). This again proceeded to completion overnight, at which point yet another sample of substrate was added. This third sample only reached about 50% conversion. The reasons for this loss of activity may be similar to those listed above: impurities accumulated through successive additions of monomer, competitive product inhibition, and changing concentrations of catalyst and CO.

Example 15

Catalyst Thermal Stability

Thermo-Gravimetric Analysis ("TGA") experiments

In order to evaluate the stability of the catalyst to potential distillation conditions, we first set out to study the thermal decomposition of the catalyst by itself. TGA was used to study the decomposition of the [(ClTPP)Al][Co(CO)$_4$], and a decomposition resulting in ~24% mass loss starts at around 150° C. and is complete by around 210° C.

Decomposition Studies

This thermal decomposition behavior was verified by heating the material in a Schlenk tube at 200° C. for 2 days. Elemental analysis of this decomposed compound showed lower carbon and hydrogen content, and higher nitrogen and aluminum content than either the initial compound or the theoretically calculated values (Table 24). The $^1$H NMR spectrum shows a mixture of peaks corresponding to the known catalyst and new peaks. In addition, the material that was heated exhibited a 98% loss in catalytic activity.

TABLE 18

Carbonylation of PO in THF with thermally decomposed catalyst.

| Catalyst | Purification | C (wt %) | H (wt %) | N (wt %) | Al (wt %) | TOF[a] |
|---|---|---|---|---|---|---|
| 37-019 | Precipitation | 57.21 | 3.95 | 4.82 | 2.40 | 254 |
|  | Theoretical | 61.56 | 3.69 | 5.13 | 2.47 |  |
| 26-286 | Heat at 200° C. | 51.33 | 3.38 | 5.65 | 2.71 | 4.7 |

[a] Reaction conditions: Endeavor reactor, [PO] = 1.8M, [PO]:[cat] = 500, 40° C., 400 psi, THF.

Preliminary Heat Cycles

Carrying the thermal decomposition study further, we prepared a catalyst solution in the given solvent and preheated the solution to 90° C. (a convenient temperature for vacuum distillation). The solution was then cooled, propylene oxide was added, and carbonylation carried out as usual. In the case of both THF and sulfolane, activity was comparable after a preheat period to the non-heated reaction.

TABLE 19

Carbonylation of PO with a preheat cycle.

| Entry | Solvent | [PO]: [cat] | Preheat time (min) | Preheat temp (° C.) | Rxn temp (° C.) | CO pressure (psi) | Time (h) | TON (mol BBL/ mol cat) | % yield |
|---|---|---|---|---|---|---|---|---|---|
| 1 | THF | 1500 | 0 | NA | 55 | 200 | 3 | 1489 | 99 |
| 2 | THF | 1500 | 60 | 90 | 55 | 200 | 3 | 1460 | 97 |
| 3 | Sulfolane | 500 | 0 | NA | 60 | 400 | 3 | 500 | 99 |
| 4 | Sulfolane | 500 | 30 | 90 | 60 | 400 | 3 | 500 | 99 |

[a] Reaction conditions: Parr reactor, [PO] = 1.8M. For preheat cycles, the catalyst and solvent were heated under $N_2$.

Recycle

An apparatus for the distillation of lactone product directly from the Parr reactor was constructed.

Even though there is more than a 30° C. boiling point differential between the lactone and the dibasic ester solvent, this simple apparatus did not give a clean distillation. In fact more than half of the solvent in the reactor distilled with the lactone product. For this reason, sulfolane (bp=296° C.) was chosen as the solvent for the initial catalyst recycling studies (Table 26). The carbonylation conditions were held constant, at 60 C and 400 psi CO, while the distillation temperature following the reaction was steadily increased after each cycle. Catalyst activity appears to be maintained after distillations at 90 and 100° C., but suffers markedly after distillation at 110° C.

TABLE 20

Carbonylation of PO in sulfolane with recycles.[a]

| Cycle | Time (h) | Turnovers (mol BBL/mol cat) | Distill time (min) | Distill temp (° C.) | Yield (g) |
|---|---|---|---|---|---|
| 1 | 1 | 90 | 30 | 90 | 5 |
| 2 | 1 | 173 | 30 | 100 | 15 |
| 3 | 1 | 102 | 30 | 110 | 7 |
| 4 | 15 | 34 | 30 | 100 | 1 |

[a]Reaction conditions: Parr reactor, [PO] = 1.8M, [PO]: [cat] = 250, 60° C., 400 psi, sulfolane.

Figure 15:
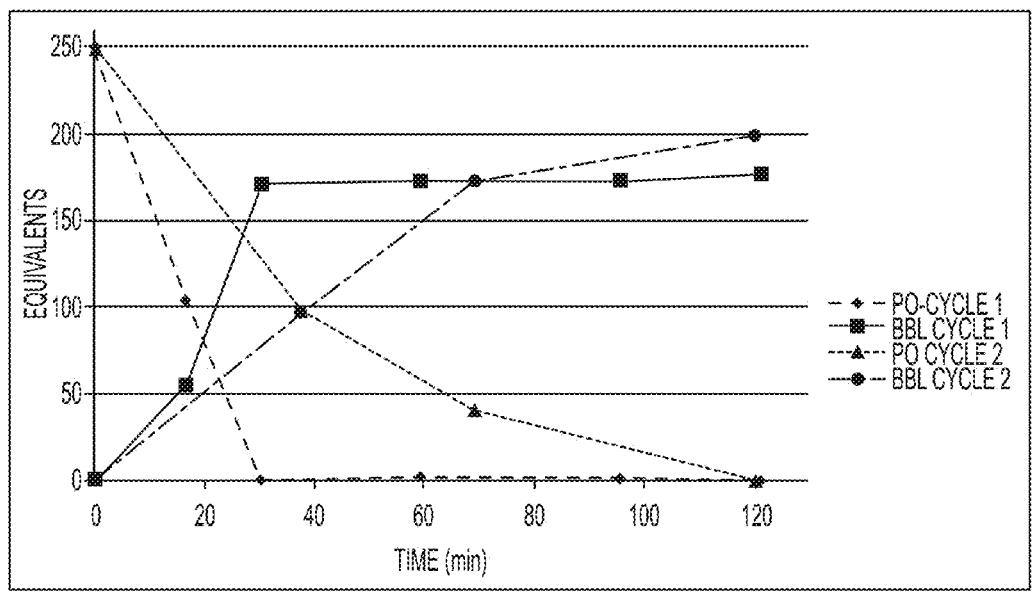
FIG. 15 is a graph of the concentrations of propylene oxide ("PO"), beta-butyrolactone during a series of carbonylation reactions with varying amounts of beta-lactone recycling. Reaction conditions: Parr reactor, [PO]=1.8 M, [PO]:[cat]=250, 60° C., 400 psi, sulfolane. Product was distilled from the reaction mixture at 90° C. under full vacuum after the first cycle.

A second recycle experiment in sulfolane with sampling during the reaction is shown below in FIG. 15. Activity appears to be somewhat less during the second cycle, following distillation at 90 C for 35 minutes, and complete conversion was not attained. However, analysis of sulfolane solutions by NMR is greatly complicated due to the fact that our typical internal standards are insoluble in sulfolane, and the sulfolane peaks coincide with the byproduct peaks we expect.

Example 16

NMR Spectroscopy

Figure 16:
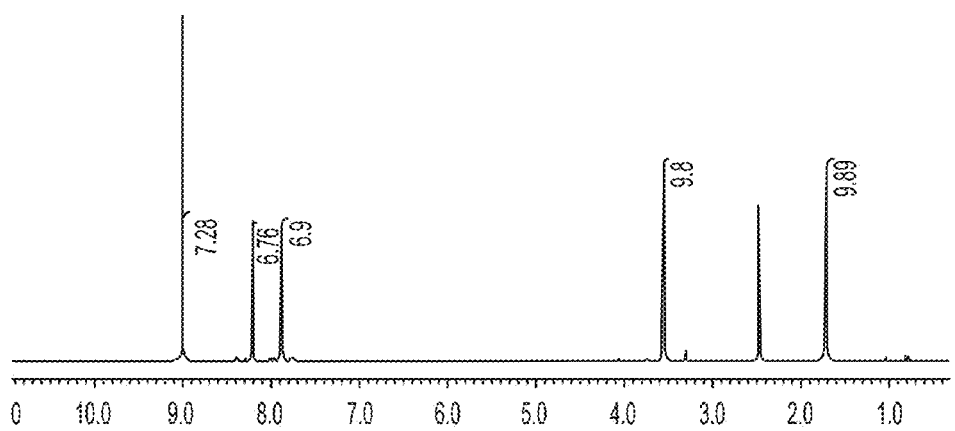
FIG. 16 shows an 1H NMR spectrum (400 MHz, DMSO-d6) of [(Cl-TPP)Al][Co(CO)4].

NMR spectroscopy has been a standard method of analysis for some time (FIG. 16). For the most part, however, the only useful information which comes from this spectrum is the amount of THF in the catalyst. Two THF molecules are bound to the Al center, and additional molecules (typically 0.2 to 1.0) may result from incomplete drying.

Example 17

Infrared Spectroscopy

Figure 17:
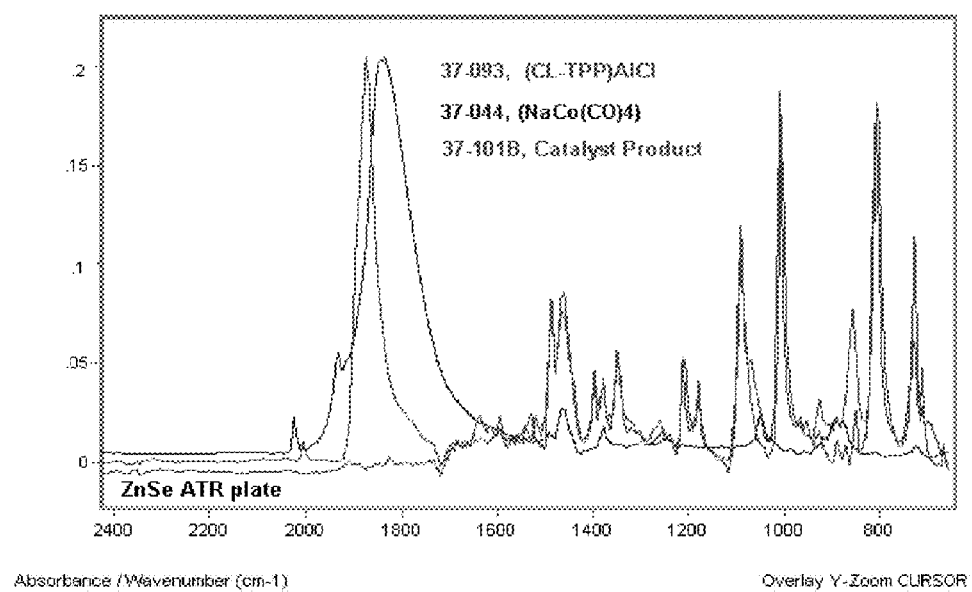
FIG. 17 shows the infrared spectra of (Cl-TPP)AlCl, NaCo(CO)4, and [(Cl-TPP)Al][Co(CO)4].

The $Co(CO)_4$ component of the catalyst has a strong absorbance at 1888 $cm^{-1}$. The $NaCo(CO)4$ starting material has a peak which is shifted from this. FIG. 17 shows an overlay of the catalyst product and the two starting materials. A peak at ~465 $cm^{-1}$ is expected for the Al—Cl bond in the (Cl-TPP)AlCl starting material, however data below 600 $cm^{-1}$ is cut off.

Example 18

Catalyst Stability

Design of a continuous process for the carbonylation of ethylene oxide to form propiolactone requires a catalyst which maintains activity for a significant amount of time. There are a number of factors which may influence the long-term stability of the catalyst, including temperature, solvent, impurities, and material compatibility.

Carbonylation: The carbonylation reaction is shown in Scheme 8 below. Coordination of an epoxide to the Lewis acid $Al^+$ center, followed by nucleophilic attack on the epoxide by the $[Co(CO)_4]^-$ anion leads to ring opening of the epoxide (2). CO insertion is typically swift to form the Co-acyl 3, which is the resting state of the catalyst in THF. Ring closing of the lactone is the rate determining step in THF, followed by loss of the lactone and coordination of another solvent molecule to reform the ion pair 1. At high temperatures and low CO concentrations, however, 2 can undergo β-hydrogen elimination to form a ketone molecule, which is a fast and exothermic reaction. In certain solvents, the lactone can undergo subsequent carbonylation to an anhydride molecule. This typically occurs at high temperatures and when the concentration of epoxide becomes very low. The formation of anhydride is also solvent dependent, being very fast in DBE, and almost non-existent in THF and sulfolane.

Scheme 8 Carbonylation of epoxides with [(ClTPP)Al]⁺[Co(CO)4]⁻.

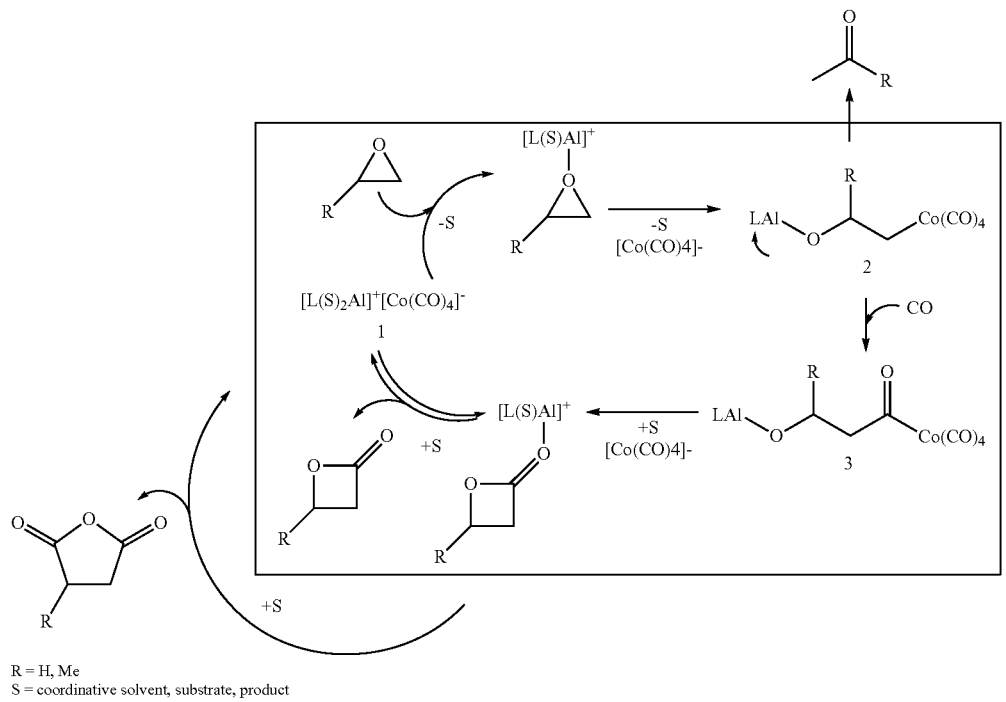

R = H, Me
S = coordinative solvent, substrate, product

Catalyst thermal stability In order to assess the catalyst's thermal stability, the catalyst was heated under $N_2$ in a Schlenk tube and the resulting material was tested for PO carbonylation activity in the Endeavor reactor (Table 29) in order to determine the importance of both temperature and time on the catalyst activity. Under the conditions of the study most of the catalyst residues maintained their activities (entries 2-5, in table 29). Only the catalysts exposed to high temperatures for long times (entries 6 and 7) resulted in a material with low activity. It appears that the catalyst can withstand high temperatures so long as it is for less than 5 hours. ¹H NMR spectroscopy of the material from entry 6 showed broad aromatic peaks and what appears to be a formula of [(ClTPP)Al][Co(CO)4](THF), where the starting catalyst (entry 1) has a formula of [(ClTPP)Al][Co(CO)4](THF)$_{2.5}$ by NMR. The material produced in entry 7 unfortunately was insoluble so NMR analysis was impossible.

TABLE 21

Carbonylation of PO with catalyst that have been preheated.[a]

| Entry | Preheat temp (° C.) | Preheat time (h) | BBL equiv | PO equiv | TOF (h⁻¹) |
|---|---|---|---|---|---|
| 1 | NA | NA | 506 | 22 | 253 |
| 2 | 100 | 1.25 | 495 | 0 | 248 |
| 3 | 100 | 5 | 484 | 33 | 242 |
| 4 | 140 | 3.88 | 528 | 2 | 264 |
| 5 | 180 | 1.38 | 474 | 15 | 237 |
| 6 | 180 | 5 | 285 | 131 | 143 |
| 7[b] | 200 | 48 | 14 | 439 | 4.7 |

[a]Catalyst heated under $N_2$ for given time at given temperature. PO carbonylation conditions: Endeavor reactor, [PO] = 1.8M, [PO]:[cat] = 500, THF 40° C., 200 psi, 2 h.
[b]Reaction time = 3 h.

Example 19

React-IR Monitoring

Figure 18:
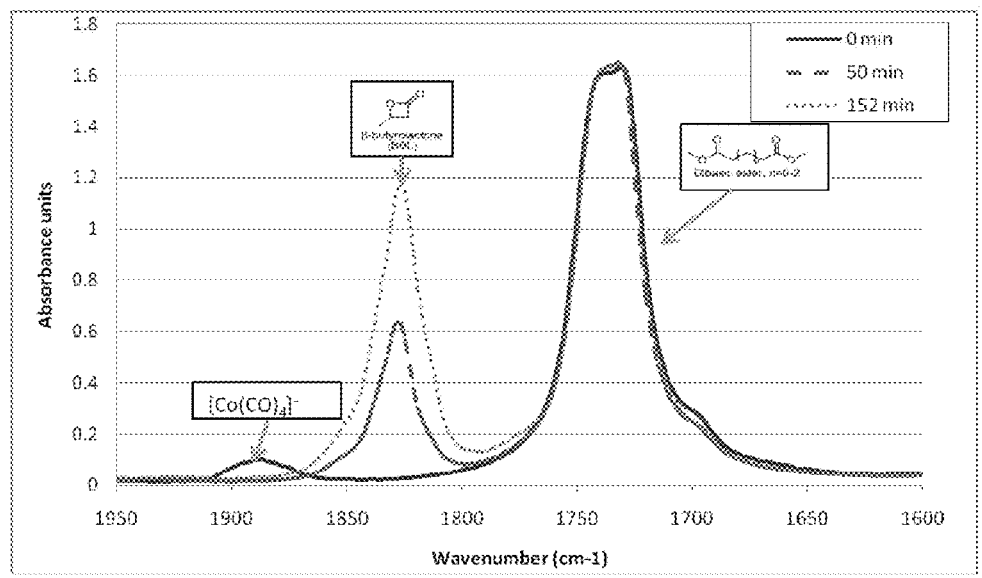
FIG. 18 is a graph of the infrared spectra of reaction solution in the carbonylation of propylene oxide in DBE-3 ([Co]=15 mM, [PO]=2.86 M, [PO]:[Co]=200, 30° C., 400 psi CO)
Figure 19:
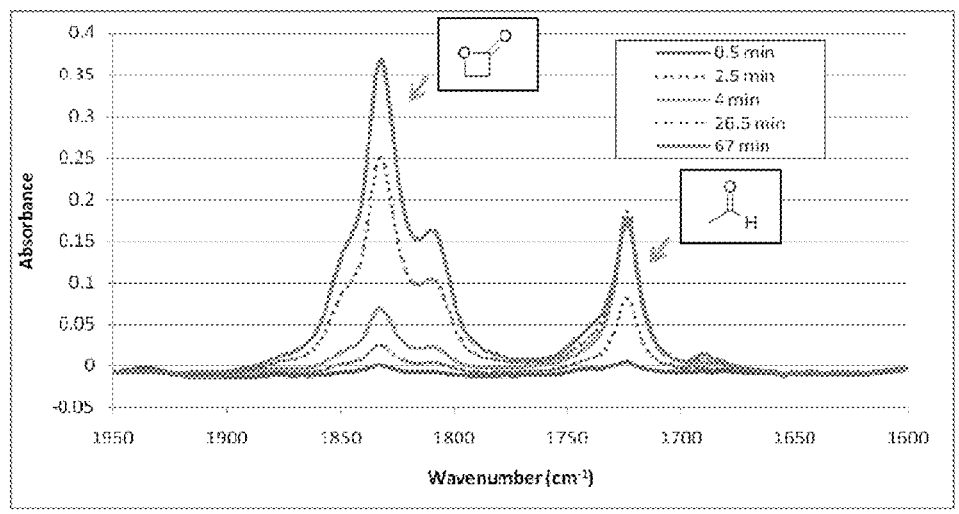
FIG. 19 is a graph of the infrared spectra of reaction solution in the carbonylation of ethylene oxide in sulfolane at various reaction times ([Co]=3.6 mM, [EO]=1.8 M, [EO]:[Co]=500, 80° C., 400 psi CO)

Representative spectra in the carbonylation of propylene oxide and ethylene oxide are shown in FIGS. 18 and 19, respectively. Formation of the product lactone can be monitored (1827 cm⁻¹ for BBL and 1836 cm⁻¹ for PL), as well as the formation of the ketone and anhydride byproducts. It is also possible to track the catalyst form, with a peak at 1887 cm-1 corresponding the catalyst 1, and a peak at 1715 cm⁻¹ corresponding to the Co acyl 3. In DBE the peak for 1 disappears rapidly (<15 seconds) upon the addition of epoxide, and the appearance of 3 is difficult to observe, as it coincides with peaks for the ketone as well as the ester groups in DBE. In sulfolane, no peak at 1887 cm⁻¹ is observable, however a number of other peaks in the 1570-1700 cm⁻¹ region have been noted but have yet to be identified.

Example 20

Solvent Stability

Catalyst stability in DBE-3 was evaluated by monitoring the IR spectrum of the solution under $N_2$ for 18 h. The peak at 1887 cm⁻¹ corresponding to the [Co(CO)$_4$]⁻ remained constant during that time period. PO and CO were added to the catalyst solution, and carbonylation went to completion in 2.5 h. At the end of the cycle, the [Co(CO)$_4$]⁻ peak returned at 79% of its original value (concentration corrections due to the addition of PO have been accounted for). However during the distillation this peak appeared to decay, and a subsequent addition of PO resulted in poor carbonylation activity.

Example 21

Pressure Effects

Figure 20:
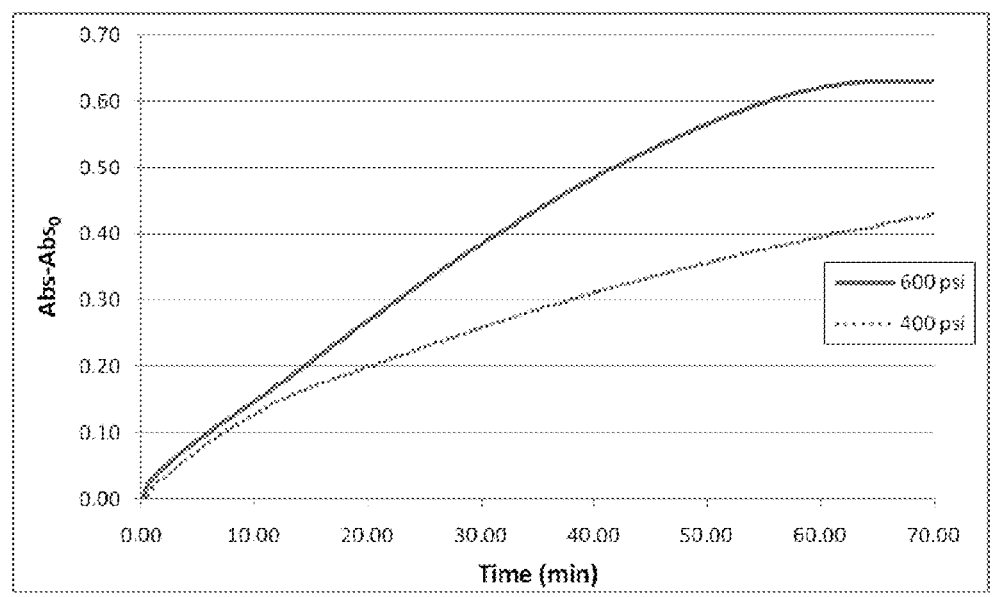
FIG. 20 shows infrared absorbance during reaction progress monitoring by in situ IR in the reaction of ethylene oxide in sulfolane ([Co]=3.6 mM, [EO]=1.8 M, [EO]:[Co]= 500, 65° C.).

In a previous DOE set of experiments of the carbonylation of EO in DBE, a pressure effect has not been observed, and so for the most part we had used 400 psi and largely ignored any potential pressure effect. At least in sulfolane, however, we determined that while initial rates were similar, over time the reaction at 600 psi performed much better than the one at 400 psi (FIG. 20).

Example 22

Temperature

Figure 21:
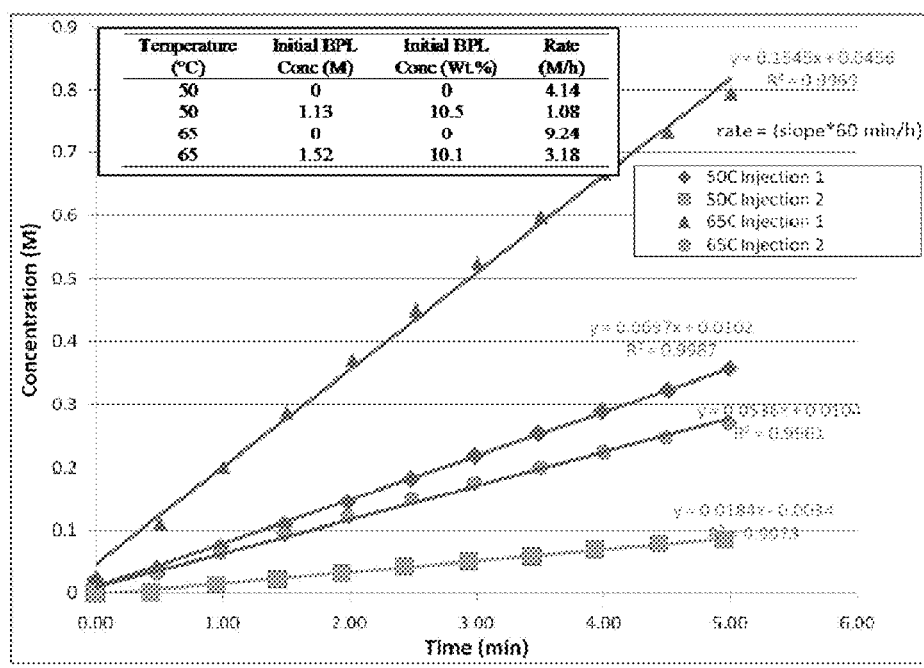
FIG. 21 shows initial rates monitored by in situ IR in the reaction of ethylene oxide in THF and sulfolane ([Co]=3.6 mM, [EO]=1.8 M, 600 psi CO).

A comparison of reaction temperatures was performed to help determine the optimal conditions for the catalyst test unit. The results of this test are shown below in FIG. 21. At 50° C. and 65° C., the reaction was performed with duplicate injections of EO (both 1.8 M). The rates at 65° C. are more than double the rates at 50° C. FIG. 21 illustrate the comparison of conditions and resulting reaction rates.

We claim:

1. A continuous method of making poly(3-hydroxy propionic acid) from ethylene oxide, the method comprising steps of:
reacting the contents of a feed stream comprising ethylene oxide, a solvent, a carbonylation catalyst and carbon monoxide to produce a liquid reaction product stream comprising beta-propiolactone and a carbonylation catalyst;
separating at least a portion of the beta-propiolactone in the reaction product stream from the carbonylation catalyst to produce a liquid catalyst recycling stream comprising carbonylation catalyst;
polymerizing at least a portion of the separated beta-propiolactone to produce poly(3-hydroxy propionic acid); and
adding the liquid catalyst recycling stream to the feed stream.

2. A continuous method of making poly(3-hydroxy propionic acid) from ethylene oxide, the method comprising steps of:
reacting the contents of a feed stream comprising ethylene oxide, a solvent, a carbonylation catalyst and carbon monoxide to produce a liquid reaction product stream comprising beta-propiolactone and a carbonylation catalyst;
returning the liquid reaction product stream to the feed stream until the weight percent of beta-propiolactone in the liquid reaction product stream is in the range of about 10% to about 90%; and
then separating at least a portion of the beta-propiolactone in the reaction product stream from the carbonylation catalyst to produce a liquid catalyst recycling stream comprising carbonylation catalyst;
polymerizing at least a portion of the separated beta-propiolactone to produce poly(3-hydroxy propionic acid); and
adding the liquid catalyst recycling stream to the feed stream.

3. The method of claim 1, further comprising treating the poly(3-hydroxy propionic acid) under conditions to convert the poly(3-hydroxy propionic acid) into a compound selected from the group consisting of acrylic acid, acrylates, acrylamide, and polyacrylates.

4. The method of claim 1, further comprising treating the poly(3-hydroxy propionic acid) under conditions to convert the poly(3-hydroxy propionic acid) into a compound selected from the group consisting of acrylic acid, methyl acrylate, ethyl acrylate, n-butyl acrylate, isobutyl acrylate, and 2-ethylhexyl acrylate.

5. The method of claim 1, further comprising treating the poly(3-hydroxy propionic acid) under conditions to convert the poly(3-hydroxy propionic acid) into acrylic acid.

6. The method of claim 1, wherein, upon reacting, the solvent has a boiling point that is higher than the boiling point of the beta-propiolactone when the solvent and beta-propiolactone are at the same pressure.

7. The method of claim 1, wherein the liquid catalyst recycling stream comprises beta-propiolactone.

8. The method of claim 1, wherein the liquid reaction product stream comprises ethylene oxide.

9. The method of claim 8, wherein the liquid reaction product stream comprises an amount of ethylene oxide sufficient to prevent anhydride formation.

10. The method of claim 9, wherein the liquid reaction product stream comprises at least about 0.1% ethylene oxide by weight.

11. The method of claim 1, further comprising treating the liquid catalyst recycling stream, prior to the adding step, by adding fresh carbonylation catalyst, removing spent carbonylation catalyst, adding solvent, adding ethylene oxide, adding a portion of the separated beta-propiolactone, or a combination thereof.

12. The method of claim 1, wherein the separating step comprises volatilizing at least a portion of the beta-propiolactone from the liquid reaction product stream to produce the separated beta-propiolactone.

13. The method of claim 1, wherein the separating step comprises exposing the liquid reaction product stream to reduced pressure.

14. The method of claim 13, wherein the reduced pressure is between about 5 Torr and about 500 Torr.

15. The method of claim 13, wherein the reduced pressure is between about 10 Torr and about 100 Torr.

16. The method of claim 13, wherein the reduced pressure is sufficient to reduce the boiling point of the beta-propiolactone by about 20 to about 100° C. below its boiling point at atmospheric pressure.

17. The method of claim 1, wherein the separating step comprises exposing the liquid reaction product stream to elevated temperature.

18. The method of claim 17, wherein the elevated temperature is greater than the boiling point of the beta-propiolactone but less than the boiling point of the solvent.

19. The method of claim 1, wherein the separating step comprises exposing the liquid reaction product stream to reduced pressure and elevated temperature.

20. The method of claim 12, further comprising a step of condensing beta-propiolactone from the separated beta-propiolactone.

21. The method of claim 1, further comprising adding beta-propiolactone to the feed stream.

22. The method of claim 21, wherein the beta-propiolactone added to the feed stream is taken from the separated beta-propiolactone.

23. The method of claim 22, wherein the beta-propiolactone is added to the feed stream until the weight percent of beta-propiolactone in the liquid reaction product stream is in the range of about 10% to about 90%, and the method then comprises withdrawing beta-propiolactone from the liquid reaction product stream while maintaining the weight percent of beta-propiolactone in the liquid reaction product stream in the range of about 10% to about 90%.

24. The method of claim 1, wherein the boiling point of the solvent is at least 20° C. higher than the boiling point of the beta-propiolactone.

25. The method of claim 1, wherein the solvent has a boiling point of at least 172° C. at atmospheric pressure.

26. The method of claim 1, wherein the carbonylation catalyst comprises a metal carbonyl compound.

27. The method of claim 26, wherein the metal carbonyl compound has the general formula $[QM_y(CO)_w]^x$, where: Q is any ligand and need not be present;

M is a metal atom;

y is an integer from 1 to 6 inclusive;

w is a number that provides a metal carbonyl compound that is stable; and x is an integer from −3 to +3 inclusive.

28. The method of claim 27, wherein M is selected from the group consisting of Ti, Cr, Mn, Fe, Ru, Co, Rh, Ni, Pd, Cu, Zn, Al, Ga and In.

29. The method of claim 27, wherein M is Co.

30. The method of claim 27, wherein M is Co, y is 1, and w is 4.

31. The method of claim 27, wherein the metal carbonyl compound comprises a carbonyl cobaltate and the carbonylation catalyst further comprises a Lewis acidic co-catalyst which comprises a metal-centered cationic Lewis acid.

32. The method of claim 31, wherein the metal-centered cationic Lewis acid comprises an aluminum cation.

33. The method of claim 1, wherein the liquid reaction product stream comprises carbon monoxide and ethylene oxide and the separating step comprises:

separating the liquid reaction product stream into i) a gaseous stream comprising carbon monoxide and ethylene oxide, and ii) a liquid stream comprising beta-propiolactone and carbonylation catalyst; and separating the liquid stream comprising beta-propiolactone and carbonylation catalyst into i) the separated beta-propiolactone; and ii) the liquid catalyst recycling stream comprising carbonylation catalyst.

34. The method of claim 33, wherein the solvent has a boiling point higher than the boiling point of the beta-propiolactone and the catalyst recycling stream further comprises solvent.

35. The method of claim 33, further comprising the step of returning the gaseous stream comprising carbon monoxide and ethylene oxide to the feed stream.

36. The method of claim 33, wherein the solvent has a boiling point lower than the boiling point of the beta-propiolactone and the gaseous stream comprising carbon monoxide and ethylene oxide further comprises solvent.

37. The method of claim 2, wherein the liquid reaction product stream is returned to the feed stream until the weight percent of beta-propiolactone in the liquid reaction product stream is in the range of about 43% to about 53%, and the method then comprises withdrawing beta-propiolactone from the liquid reaction product stream while maintaining the weight percent of beta-propiolactone in the liquid reaction product stream in the range of about 43% to about 53%.

38. The method of claim 1, wherein the separated beta-propiolactone is gaseous.

39. The method of claim 2, wherein the separated beta-propiolactone is gaseous.

\* \* \* \* \*